United States Patent [19]
Hughes, Jr. et al.

[11] Patent Number: 5,962,021
[45] Date of Patent: *Oct. 5, 1999

[54] COMBINED PHARMACEUTICAL ESTROGEN-ANDROGEN-PROGESTIN ORAL CONTRACEPTIVE

[75] Inventors: Claude L. Hughes, Jr., Ventura, Calif.; Manuel J. Jayo, Advance, N.C.

[73] Assignee: Wake Forest Universtiy, Winston-Salem, N.C.

[*] Notice: This patent is subject to a terminal disclaimer.

[21] Appl. No.: 09/102,707

[22] Filed: Jun. 22, 1998

Related U.S. Application Data

[63] Continuation of application No. 08/679,764, Jul. 10, 1996, Pat. No. 5,770,226.

[51] Int. Cl.$^6$ .............................. A61K 9/20; A61K 31/56
[52] U.S. Cl. ........................ 424/464; 424/449; 514/170; 514/841; 514/843
[58] Field of Search ...................... 424/464, 449; 514/841, 843, 170

[56] References Cited

U.S. PATENT DOCUMENTS 5,770,226  6/1998  Hughes et al. ........................ 424/464

*Primary Examiner*—Thurman K. Page
*Assistant Examiner*—James M. Spear
*Attorney, Agent, or Firm*—Timothy S. Corder; Vinson & Elkins L.L.P.

[57] ABSTRACT

Disclosed are methods and compositions for oral contraception and hormonal therapy. Certain compositions and methods of the invention contain androgens, and preferably methyltestosterone to be combined with estrogen and progestin compositions in a hormonal component of a pharmaceutical composition.

94 Claims, No Drawings

COMBINED PHARMACEUTICAL ESTROGEN-ANDROGEN-PROGESTIN ORAL CONTRACEPTIVE

This application is a continuation of application U.S. Ser. No. 08/679,764 filed Jul. 10, 1996, U.S. Pat. No. 5,770,226, the entire specification and claims of which are incorporated herein by reference.

BACKGROUND OF THE INVENTION

1. Field of the Invention

The present invention relates generally to the field of pharmaceutical preparations and in particular to the field of oral contraceptives. In particular the present invention addresses the field of peak bone mass accrual in young oral contraceptive users.

2. Description of the Related Art

Due to the relatively high rate of teenage pregnancy in the United States, pediatric and adolescent gynecologists often recommend that young women take some form of contraception to prevent unwanted pregnancies (The Contraception Report, 1995). The most common method of contraception among adolescents is oral contraceptives, taken by approximately 46% of the sexually active population. Consequently, almost half of all premenopausal women (<44 years) are potentially taking oral contraceptives while their skeleton is still maturing and before reaching peak bone mass, which occurs at about age 30–35. Peak bone mass is a term rat describes a point at which the maximum bone density is reached. For a woman, bone density increases until about age 30–35, and then slowly decreases for the remainder of her life. This peak is known as the peak bone mass. As the bone density decreases in later years, osteoporosis or bone breakage are more likely to occur. It is important, therefore, to forestall these problems by attaining as high a peak as possible.

Although estrogen is necessary for maintaining bone density in premenopausal women, the role of androgens or their combined effect is unclear. It is generally accepted that low-dose estrogens are potent bone growth promoters and probably provide the major growth stimulus in girls, while in boys, estrogens may be involved in the growth spurt along with testosterone (Kulin, 1991). However, some recent evidence suggests that androgens play an important role in building and maintaining bone in the female as well as in the male. During puberty, androgens influence bone growth and peak bone mass, but after puberty, during adolescence and early adulthood, androgens are also involved in the maintenance of bone mass. Peak bone mass is acquired by age 30–35 (Recker, et al., 1992), but 15% of the adult height and 48% of the skeletal mass are attained during adolescence.

Unfortunately, oral contraceptive treatment, like oophorectomy, causes a significant decrease in androgen levels and consequently oral contraceptives are commonly used to treat hirsutism in women (Carr, et al., 1995). Young women with hyperandrogenemia show increased levels of luteinizing hormone (LH) and free testosterone to total testosterone ratio (fT)/T, and a decreased serum level of sex hormone-binding globulin (SHBG). Low-dose oral contraceptives reduce the hormone imbalance and hyperandrogenemia (Yamamoto and Okada, 1994; Rosenfield and Lucky, 1993). Interestingly, not only does oral contraceptive therapy lower serum A, T and fT in hyperandrogenic women, but estradiol ($E_2$) levels also significantly decrease with oral contraceptive therapy.

Among the first orally active steroids to be used in inhibiting ovulation, some had inherent estrogenic activity and some preparations of progestins were later found to be contaminated with estrogen. This suggested that estrogen enhanced the suppressive effect of the progestin and led to the general use of a mixture of the two. A comprehensive investigation of the inhibition of ovulation by the use of progestational agents was initiated by Rock, Pincus, and Garcia. The study showed that ovulation could be abolished at will for as long as desired and with great regularity (Rock et al., 1957; Pincus, 1960). The compounds used were derivatives of 19-nortestosterone, given by mouth from day 5 to day 25 of the menstrual cycle (the first day of menses is day 1).

The most common type of oral contraceptive is the combination preparation, which contains both an estrogen and a progestin. Experience with these preparations shows them to be 99 to 100% effective. This method of reversible contraception is, then, the most effective yet devised. Other modifications of steroidal contraception have also been tried with success. Sequential preparations, in which an estrogen is taken for 14 to 16 days and a combination of an estrogen and a progestin is then taken for 5 or 6 days, have been about 98 to 99% successful as oral contraceptives. However, because of reports suggesting an increased incidence of endometrial tumors and a lower efficacy, sequential preparations of this type have been removed from the market. They have been replaced by products that contain estrogen and relatively low amounts of a progestin that varies during the monthly cycle. Biphasic and triphasic formulations of sequential preparations of oral contraceptives are listed in Table 1. These preparations have been developed in attempts to lower the total amounts of hormone given and thus to reduce the incidence and severity of side effects.

The relationship between oral contraceptive use and skeletal health has been examined in a number of human studies. Tuppurainen, et al. (1994) studied the effects of oral contraceptive use on BMD in perimenopausal women (48–60 years). Twenty-nine percent of the women were past users of oral contraceptives. Oral contraceptive users (n=939) had a slightly higher (but statistically significant) lumbar BMD than non-users (n=2283). The study with the largest number of subjects (the Oral Contraception Study of the Royal College of General Practitioners, n=46,000 women) was carried out between 1968 and 1990 and examined the relationship between oral contraceptive use and subsequent incidence of first fractures (excluding skull, rib, and multiple fractures) in married or living as married women (Cooper, et al., 1993). After adjustment for age, parity, cigarette smoking, and socioeconomic class, women who had ever used oral contraceptives were found to be at significantly higher risk for subsequent fractures (relative risk 1.20) compared to women who had never used oral contraceptives. Thus, this very large prospective study suggests that oral contraceptive use does not promote long term skeletal health and may even be detrimental in terms of fracture risk.

While the majority of studies in humans have utilized female populations with age ranges well into the postmenopausal years, a few studies have focused on "younger" females who have not yet attained peak bone mass. In a longitudinal study of 156 pre-menopausal women aged 20–30, Recker, et al. (1992) found a positive association between oral contraceptive use and whole body bone mass, but no association with lumbar spine (L2–L4) or forearm bone mass. Lindsay, et al. (1986) reported results from 2 cross-sectional studies, one of which involved 57 healthy premenopausal women between 25 and 35 years of age, 24 of which had previously taken oral contraceptives (30 or 50 mg ethinyl estradiol along with norgestrel) for more than 6 months. None of the subjects was taking oral contraceptives at the time of the study. Previous oral contraceptive use was associated with increased BMD in the lumbar spine but not in the radius. The second cross-sectional study showed no association between oral contraceptive use on lumbar spine BMD in 14 postmenopausal women compared to 24 age-matched controls.

In a cross-sectional study of 60 women aged 24–35, Kanders, et al. (1984) found that oral contraceptive users (greater than 5 months use) had a significantly higher spinal BMD than non-users. Goldsmith and Johnston (1975) examined the relationship between oral contraceptive use and distal radius bone mineral among different populations of women in a large cross-sectional study carried out in 1969 and 1970, when most of the oral contraceptive users aged 20–29 were taking mestranol (n=219) and relatively few were taking ethinyl estradiol (n=47). High dose mestranol use (>100 mg/day) was associated with increased radial bone mass, while ethinyl estradiol (50 or 100 mg/day) use and radial bone mass were not associated in white women (n=65) and were negatively associated in black women (n=11).

Stevenson, et al. (1989) found no association between oral contraceptive use and bone density at several sites, including lumbar spine, in 112 premenopausal women aged 21–52 (median age=34.1). However, positive associations were found between bone density at these same sites and oral contraceptive use in 172 postmenopausal women aged 28–68 (median age=53.4). Mazess and Barden (1991) found no relationship between oral contraceptive use and BMD of the spine, radius, or femoral neck in a study of 200–300 healthy women of 20–39 years of age. Recently, Hansen (1994) studied 249 healthy premenopausal women aged 21 to 51 (17 were <30 years of age) and reported no association of oral contraceptive use with bone density at a number of skeletal sites, although a significant reduction (<32%) in BGP was observed in current oral contraceptive users compared to never users In a recent study, young women using oral contraceptives did not gain spinal bone density over time (Carr, et al., 1995). According to their reported age (mean age of 26±1 yr) and using regression lines reported by Recker, et al. (1992), bone mass in most of the women in this study should have been increasing during the study period, ending with a positive balance. Also, Teegarden, et al. (1995), investigated the interaction between oral contraceptive use and exercise in women ages 18 to 31 years. Surprisingly, after 6 months, women who were exercising and using oral contraceptives lost a significant amount of spinal bone mineral density (BMD), whereas women not exercising and taking oral contraceptives gained a significant amount of spinal BMD. Serum concentrations of hormones were not reported (Teegarden, et al., 1995). These results suggest serious consequences. If young women who exercise and take oral contraceptives fail to gain bone during their adolescent and young adult years (ages 15 to 30 years), they will attain a lower than expected peak bone mass. Therefore, age-related and postmenopausal bone loss will have a greater effect on bone mass and a fracture threshold may be reached earlier in life.

There is an immediate need therefore, for an oral contraceptive, especially for women in their teens and twenties, that is effective to prevent unwanted pregnancies and still allows the attainment of normal peak bone mass.

SUMMARY OF THE INVENTION

The present invention may be described in a general sense as novel compositions and methods for oral contraception. These compositions and methods of the present invention provide improvements over prior methods of oral contraception in that an androgen is included in certain of the formulations in order to mitigate a decrease in bone accrual in younger users of oral contraceptives. It is an important finding by the present inventors that younger users of estrogen containing oral contraceptives may not attain as high a level of bone mineralization at peak bone mass (around the age of 30–35) as they may have achieved without oral contraceptive use. This effect may lead to problems such as osteoporosis or broken bones later in life. It is a further finding of the present inventors that this effect may be antagonized by the addition of an androgen to the oral contraceptive formulation, especially the formulations to be used by women who have not yet reached peak bone mass. However, the formulations may be used by oral contraceptive users of any age to restore a more natural estrogen/androgen balance.

The invention may be described in certain broad aspects as a contraceptive preparation comprising estrogen and progestin and an androgen in an amount effective to decrease the loss of bone accretion in a user of oral contraceptives. The androgen may be any androgen known in the art that is suitable for use in an oral contraceptive preparation and is preferably a testosterone and more preferably methyltestosterone. Representative androgens that are currently available are shown in Table 2. It is understood that any of these formulations that are adaptable to an oral contraceptive would be useful in the practice of the present invention. It is also understood that the use of androgen containing estrogen/progestin contraceptives to be administered in any other form, such as an implant or bolus injection would also be encompassed by the appended claims.

The dosage will depend upon the physiological reaction of the subject to the presence of an androgen in the birth control formulation, and will be monitored by the prescribing physician. For example, certain subjects such as athletes, for example, may require that their serum testosterone levels not be affected. Therefore, the physician may monitor serum testosterone over periods of about every three months, for example, to determine the correct level of testosterone to include in the oral contraceptive formulation. It is contemplated that the contraceptive formulations may be available in three or more androgen levels, and that the physician would prescribe a higher or lower androgen formulation depending on changes in serum testosterone levels in users of the oral contraceptives. It is a finding of the present inventors that a certain decrease in bone accrual will occur with the use of estrogen and progestin-containing oral contraceptives by women from the ages of puberty until about thirty to thirty five years. The present compositions will enhance bone accrual, or in other words, will mitigate a negative effect associated with oral contraceptive use in women of this age group. Any such enhancement or mitigation is an improvement over the prior art, even if normal peak bone mass is not attained. It is an objective of the invention, however, to restore near normal, or even normal bone accrual, and thus peak bone mass, in oral contraceptive users.

Certain formulations of the invention will contain from about 0.2 milligrams to about 1.5 milligrams methyltestosterone per daily dose. The formulations may contain for example, 0.2, 0.3, 0.4, 0.5, 0.6, 0.7, 0.8, 0.9, 1.0, 1.1, 1.2, 1.3, 1.4 or 1.5 milligrams methyltestosterone per daily dose. The use of the term "about" 0.2 to 1.5 milligrams indicates that dosages slightly outside this range may also be effective and safe, and such formulations are also encompassed by the scope of the present claims. The preparations containing methyltestosterone are preferably administered during days 8–13 of a menstrual cycle to correspond with naturally occurring increases in testosterone levels during the menstrual cycle. For example, it is known that testosterone and estrogen levels both increase during this period of the normal cycle. The androgen or testosterone containing compositions also preferably contain an estrogen and a progestin for the prevention of conception. Preferably, the progestin is levonorgestrel present in a concentration of about 0.050 milligrams and the estrogen is ethinyl estradiol present at a concentration of about 0.03 milligrams per daily dose.

An embodiment of the present invention may be described as an oral contraceptive preparation comprising a first composition comprising methyltestosterone with levonorgestel and ethinyl estradiol to be administered daily from day 8 to about day 13 of a menstrual cycle. The contraceptive preparation also contains a second composition comprising levonorgestrel and ethinyl estradiol to be administered daily from day 14 to about day 18 following administration of the first composition. The preparation may also be defined as containing a third composition comprising levonorgestrel and ethinyl estradiol to be administered daily following administration of the second composition from about day 19 until about day 28 of a menstrual cycle. This preparation may further comprise a placebo composition to be taken during days 1–7 of the menstrual cycle. It is understood that the compositions are preferably taken on days 8–13 for the first composition, days 14–18 for the second composition, and days 19–28 for the third composition. However, the timing of administration is understood to be the best time to administer these formulations and may be varied slightly without violating the scope and spirit of the present invention. The first composition may be further defined as comprising about 0.2 milligrams to about 1.5 milligrams methyltestosterone per daily dose and about 0.05 milligrams of levonorgestrel and about 0.03 milligrams ethinyl estradiol per daily dose. The second composition may preferably be defined as about 0.075 milligrams levonorgestrel and about 0.04 milligrams ethinyl estradiol per daily dose. The third preparation may be further defined as about 0.125 milligrams levonorgestrel and about 0.03 milligrams ethinyl estradiol per daily dose.

The invention may also be described in certain embodiments as an oral contraceptive composition comprising from about 0.2 milligrams to about 1.5 milligrams methyltestosterone, about 0.05 milligrams levonorgestrel, and about 0.03 milligrams ethinyl estradiol per daily dose. In certain embodiments the invention may be described as an oral contraceptive composition formulated as 28 tablets as follows: six tablets comprising about 0.2 milligrams to about 1.5 milligrams methyltestosterone, about 0.05 milligrams levonorgestrel, and about 0.03 milligrams ethinyl estradiol; 5 tablets comprising about 0.075 milligrams levonorgestrel, and about 0.04 milligrams ethinyl estradiol; and 10 tablets comprising about 0.125 milligrams levonorgestrel, and about 0.03 milligrams ethinyl estradiol, and the composition may further comprise about 7 placebo tablets. It is understood that the placebo tablets of any of the compositions described herein may contain iron, calcium, vitamins, minerals, or other beneficial supplements to be added to the diet of the oral contraceptive user.

A method of enhancing bone accrual in a subject taking estrogen containing oral contraceptives wherein the subject has not obtained peak bone mass is also an embodiment of the present invention. The method comprises administering an androgen to the subject in conjunction with the oral contraceptives. In preferred embodiments of the method the androgen is administered as about 0.2 milligrams to about 1.5 milligrams of methyltestosterone per day for days 8–13 of the menstrual cycle. The invention may also be described as a method of preventing conception in a subject. The method comprises administering to the subject a formulation comprising about 0.2 milligrams to about 1.5 milligrams methyltestosterone, about 0.05 milligrams levonorgestrel, and about 0.03 milligrams ethinyl estradiol daily on days 8–13 of the menstrual cycle, then about 0.05 milligrams levonorgestrel and about 0.04 milligrams ethinyl estradiol daily on days 14–18 of the menstral cycle, and about 0.125 milligrams levonorgestrel and about 0.03 milligrams ethinyl estradiol daily on days 19–28 of the menstrual cycle.

An embodiment of the present invention may be described as a one month oral contraceptive pack comprising a first composition of 7 tablets comprising a placebo composition to be taken daily on days 1 to 7 of a menstrual cycle. The one month oral contraceptive pack also comprises a second composition of 6 tablets comprising about 0.2 mg to about 1.5 mg methyltestosterone, about 0.050 mg levonorgestrel and about 0.030 mg ethinyl estradiol to be taken daily on days 8–13 of a menstrual cycle. The one month oral contraceptive pack may be further defined as comprising a third composition of 5 tablets comprising about 0.075 mg levonorgestrel and about 0.040 mg ethinyl estradiol to be taken daily on days 14–18 of a menstrual cycle. The oral contraceptive pack may comprise a fourth composition of 10 tablets comprising about 0.125 mg levonorgestrel and about 0.030 mg ethinyl estradiol to be taken daily on days 19–28 of a menstrual cycle. The one month pack further comprising a dispenser comprising 28 compartments, each compartment containing an oral contraceptive composition. A typical dispenser would provide for 28 pills to be taken one a day in a determined order. Exemplary dispensers are those described in U.S. Pat. No. 4,165,709, U.S. Pat. No. 4,807,757, U.S. Pat. No. 3,678,884 or U.S. Pat. No. 3,651,927 (each incorporated herein by reference).

In other embodiments the present invention comprises a one month oral contraceptive pack comprising a first composition of 7 tablets comprising a placebo composition to be taken daily on days 1 to 7 of a menstrual cycle. The one month oral contraceptive pack also comprises a second composition of 6 tablets comprising about 0.2 mg to about 1.5 mg methyltestosterone, about 0.050 mg levonorgestrel and about 0.030 mg ethinyl estradiol to be taken daily on days 8–13 of a menstrual cycle. The one month oral contraceptive pack may be further defined as comprising a third composition of 5 tablets comprising about 0.075 mg levonorgestrel, about 0.040 mg ethinyl estradiol and about 0.2 mg to about 0.5 mg methyltestosterone to be taken daily on days 14–18 of a menstrual cycle. The oral contraceptive pack may comprises a fourth composition of 10 tablets comprising about 0.125 mg levonorgestrel, about 0.030 mg ethinyl estradiol and about 0.2 mg to about 0.5 mg methyltestosterone to be taken daily on days 19–28 of a menstrual cycle. The one month pack further comprising a dispenser comprising 28 compartments, each compartment containing an oral contraceptive composition.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

DETAILED DESCRIPTION OF THE INVENTION

The present invention provides oral contraceptives that prevent unwanted pregnancies and allow the normal accrual of bone mass in younger users of the contraceptives, so that optimal peak bone mass may be reached by those users. The present invention, then, is a safe, effective oral contraceptive that prevents certain side-effects associated with estrogen/progestin oral contraceptives, including the increased risk of osteoporosis in later life due to the lowered peak bone mass that is the result of estrogen/progestin oral contraceptive use prior to attainment of peak bone mass. The present invention provides compositions for oral contraceptives that will be most beneficial to users under the age of 30, however, the compositions will also be effective to prevent pregnancy in all premenopausal women.

The present invention arises from the discovery that oral contraceptives prevent the proper accrual of bone in young non-human female primates and that this effect can be attributed to suppression of endogenous androgen levels. This animal study strongly suggests that the same adverse effect occurs in young women (age 15 to 30 years) and due to the same mechanism (suppressed androgen levels). Diminished accrual of bone prevents attainment of maximal peak bone mass thus increasing the risk of osteoporosis later in life. The problem of poor accrual of bone mass in young women is presently caused by standard oral contraceptive preparations that contain estrogen and progestin. The compositions of the present invention include androgen in addition to estrogen and progestin, and thus offer the unique advantage of allowing normal bone accretion and the attainment of normal peak bone mass.

Preparations and Dosage of Estrogen/Progestin Oral Contraceptives

Some formulations presently used as oral contraceptives are listed in Table 1. The combined preparations contain 0.02 to 0.05 mg of ethinyl estradiol or mestranol and various amounts of a progestin, and are taken for 21 days. The next course is started 7 days after the last dose or 5 days after the onset of the menstrual flow. It should be noted that ethinyl estradiol is approximately twice as potent as mestranol.

Sequential preparations are formulated to be taken in two (biphasic) or three (triphasic) continuous phases. With biphasic preparations a fixed-dose combination of an estrogen and progestin is taken for 10 days, followed by a different fixed-dose combination of estrogen and progestin for 11 days. The pills are discontinued for 7 days before the cyclic administration is resumed. Triphasic preparations contain the same or different quantities of an estrogen and variable quantities of a progestin in three sets of tablets. Each set is taken for 5 to 10 days, depending upon the specific formulation. After 21 days of administration, the medication is discontinued for 7 days before the cycle is resumed.

TABLE 1

COMPOSITION AND DOSES OF SOME ORAL CONTRACEPTIVES

| ESTROGEN (mg) | PROGESTIN[1] (mg) | REPRESENTATIVE TRADE NAME |
|---|---|---|
| Combinations[2]: | | |
| 0.02 Ethinyl estradiol | 1.0 Norethindrone acetate | LOESTRIN 1/20 |
| 0.03 Ethinyl estradiol | 0.3 Norgestrel | LO/OVRAL |
| 0.03 Ethinyl estradiol | 1.5 Norethindrone acetate | LOESTRIN 1.5/30 |
| 0.03 Ethinyl estradiol | 0.15 Norethindrone acetate | NORDETTE |
| 0.035 Ethinyl estradiol | 0.4 Norethindrone | OVCON 35 |
| 0.035 Ethinyl estradiol | 0.5 Norethindrone | BREVICON |
| 0.035 Ethinyl estradiol | 1.0 Ethynodiol diacetate | DEMULEN 1/35 |
| 0.035 Ethinyl estradiol | 1.0 Norethindrone | ORTHO-NOVUM 1/35 |
| 0.05 Mestranol | 1.0 Norethindrone | ORTHO-NOVUM 1/50 |
| 0.05 Ethinyl estradiol | 0.5 Norgestrel | OVRAL |
| 0.05 Ethinyl estradiol | 1.0 Ethynodiol diacetate | DEMULEN 1/50 |
| 0.05 Ethinyl estradiol | 1.0 Norethindrone | OVCON 50 |
| 0.05 Ethinyl estradiol | 1.0 Norethindrone acetate | NORLESTRIN 1/50 |
| 0.05 Ethinyl estradiol | 2.5 Norethindrone acetate | NORLESTRIN 2.5/50 |
| Sequentials[3]: | | |
| 0.03, 0.04, 0.03 Ethinyl estradiol | 0.05, 0.075, 0.125 Levonorgestrel | TRI-LEVLEN |
| 0.035 Ethinyl estradiol | | TRI-NORINYL |
| 0.035 Ethinyl estradiol | 0.5, 1.0, 0.5 Norethindrone | ORTHO-NOVUM 7/7/7 |
| 0.035 Ethinyl estradiol | 0.5, 0.75, 1.0 Norethindrone 0.5, 1.0 Norethindrone | ORTHO-NOVUM 10/11 |

TABLE 1-continued

COMPOSITION AND DOSES OF SOME ORAL CONTRACEPTIVES

| ESTROGEN (mg) | PROGESTIN[1] (mg) | REPRESENTATIVE TRADE NAME |
|---|---|---|
| "Minipills"[4]: | | |
| — | 0.35 Norethindrone | MICRONOR |
| — | 0.075 Norgestrel | OVRETTE |
| Postcoital[5]: | | |
| Diethylstilbestrol | — | — |

[1]Of the progestin used, norgestrel is somewhat androgenic, while the others have minimal androgenic activity.
[2]Combination tablets are taken for 21 days and are omitted for 7 days. These preparations are listed in order of increasing content of estrogen.
[3]These preparations include fixed-dose tablets with the same or different amounts of estrogen and variable amounts of progestin. With biphasic preparations, the first set of tablet is taken for 10 days and the second for 11 days, followed by 7 days of no medication. With triphasic preparations, each set of tablets is taken for 5 to 10 days in three sequential phases, followed by 7 days of no medication.
[4]"Minipills" are taken daily continually.
[5]Diethylstilbestrol is taken in a dose of 25 mg daily twice daily for 5 days within 72 hours after sexual intercourse.

Many contraceptive preparations are dispensed in convenient calendar-like containers that help the user to count the days. Some obviate the need of counting by incorporating seven blank pills in the package to provide 3 weeks of treatment and 1 week of no treatment. A pill is taken every day, regardless of when menstruation starts or stops. Iron is included in the "blank" pills in some preparations.

The "minipills" (for example MICRONOR and NOR-QD, containing 0.35 mg of norethindrone, and OVRETTE, containing 75 $\mu$g of norgestrel) are taken daily continually. Since they are less effective and pregnancy is possible during their administration, patients should discontinue the "minipill" if they have amenorrhea for more than 45 to 60 days, and they should be examined for pregnancy. Likewise, if patients have missed one or more pills and have amenorrhea for more than 45 days, they should be similarly evaluated.

Preparations and Dosage of Androgens

Some parenteral and oral formulations of androgens available for clinical use are summarized in Table 2. Androgen therapy has been used primarily for the development and/or maintenance of secondary sex characteristics. Androgens have been administered through intramuscular preparations but may also be administered orally. Androgens of the present invention include, but are not limited to those listed in Table 2 that may be adapted for use in an oral contraceptive composition.

TABLE 2

| Non-Proprietary Name | Example of a Trade Name | Dosage Forms and Usual Dosage |
|---|---|---|
| Testosterone | Testoject-50 ™ | Aqueous suspension for intramuscular use: 10 to 50 mg three times weekly |
| Testosterone Propionate | Testex ™ | Oily solution for intramuscular use: 10 to 25 mg two or three times weekly |
| Testosterone Enanthate | Delatestyl | Oily solution for intramuscular use: 50 to 400 mg every 2 to 4 weeks |
| Testosterone Cypionate | Depo-Testosterone | Oily solution for intramuscular use: 50 to 400 mg every 2 to 4 weeks |
| Nandrolone Decanoate | Deca-Durabolin | Oily solution for intramuscular use: 50 to 100 mg every 3 to 4 weeks |
| Nandrolone Phenpropionate | Durabolin | Oily solution for intramuscular use: 50 to 100 mg weekly for breast carcinoma |
| Danazol | Danocrine | Capsules: 200 to 800 mg daily |
| Fluoxymesterone | Halotestin | Tablets: 2.5 to 20 mg daily |
| Methandrostenolone | Dianabol | Tablets: 2.5 to 5 mg daily for osteoporosis |
| Methyltestosterone | Metandren, Oreton Methyl | Tablets and Capsules: 10 to 50 mg daily. Buccal Tablets: 5 to 25 mg daily |
| Oxandrolone | Anavar | Tablets: 2.5 to 20 mg daily |
| Oxymetholone | Anadrol-50 | Tablets: 1 to 5 mg/kg daily for anemia. |
| Stanozolol | Winstrol | Tablets: 6 mg daily |
| Testolactone | Teslac | Tablets: 250 mg four times daily for breast carcinoma |

Androgenic Effects on Bone

Without being limited to any particular theory, it is contemplated that the mechanism of oral contraceptive use leading to lower peak bone mass in young women is based on the following considerations. The prime steroid produced by the ovary is androstenedione (A) from which testosterone (T) and estradiol ($E_2$) are derived peripherally. A significant proportion of circulating androgens appear to be derived from the ovary since serum T and A decrease (50%) after oophorectomy (Adashi, 1994; Hughes, et al., 1991).

a) In vitro Cellular Evidence

Androgen receptors have been identified in osteoblast-like cells (Colvard, et al., 1989; Wiren, et al., 1995) and may modulate calcium channels in bone cells (Takeuchi and Guggino, 1995). In addition, androgens stimulate osteoblast differentiation and proliferation (Kasperk, et al., 1990).

b) Evidence of Androgenic Effects on Bone in Animal Models

Androgens are believed to play a role in building and maintaining bone in the female as well as in the male. The anti-androgen drug, flutamide, inhibits responses to androgens from both the gonads and the adrenals. Osteopenia was induced in intact female rats given flutamide (15 mg/kg body weight orally daily). Bone turnover in female rats with intact ovaries was affected as measured by skeletal $^{45}$Ca changes suggesting that flutamide-mediated androgen deficiency bone thinning was caused principally by reduced bone formation (Goulding and Gold, 1993). These findings were recently reproduced in intact female rats that were given a pure non-steroidal anti-androgen (Casodex®) daily for 3 weeks. The metaphyseal bone volume and longitudinal bone growth were similar to vehicle-treated intact females. However, dynamic histophometry showed that bone formation rate was significantly reduced in the Casodex®-treated rats (Flanagan, et al., 1995).

Direct bone effects by androgens occurred when androstenedione was given to ovariectomized rats and prevented the ovariectomy-induced osteopenia via decreasing bone turnover (a, et al., 1995). In older ovariectomized rats, dihydrotestosterone (DHT) was tested because DHT, like testosterone, binds to androgen receptors, but unlike testosterone, DHT cannot be aromatized to estrogen. Both DHT and estradiol provided protection against ovariectomy-induced osteopenia in older ovariectomized rats (Vanin, et al., 1995).

Intramuscular administration of the steroidal anti-androgen cyproterone acetate in white-tailed deer immediately after velvet shedding induced: (a) dramatic reduction of testosterone levels in plasma, (b) premature casting in bucks with fully mineralized antlers and (c) renewal of bone rebuilding activity in incompletely mineralized antlers which resulted in blockage of casting (Bubenik, et al., 1987).

Hormone manipulations in female monkeys affect their body composition and bone mineral status (Jayo, et al., 1989). After one year of hormone treatment via Silastic implants, intact placebo monkeys had lower bone mass of the lumbar spine and whole skeleton than intact monkeys receiving (A+Estrone [$E_1$]) or monkeys receiving testosterone. Testosterone-treated monkeys increased in body weight significantly compared to the other two groups, but both androgen-treated groups significantly increased tibial bone strength and cortical density (Kasra and Grynpas, 1995).

c) Evidence of Androgenic Effects on Bone in Women

Direct evidence for the need of adequate androgenic stimulus in female bone status is shown by a case of a woman with androgen insensitivity that was recently described in Spain. The 17-year-old had poor bone density and elevated levels of androgens. Physicians treated the young woman with estrogens, but her lack of response to estrogen therapy suggested the importance of an androgenic stimulus even after puberty (Munoz-Torres, et al., 1995). Daniel, et al. (1992) studied the effects of cigarette smoking in young women (25 smokers, 27 nonsmokers) aged 20–35 years. Bone mineral density was not different between groups, but for both groups SHBG and free androgen index (T/SHBG) made significant p<0.05) contributions to the variance in bone density.

Adolescent black women have greater bone mass and higher levels of serum testosterone than adolescent white women (Wright, et al., 1995). In a study of elderly black women, bone mass was greater compared with elderly white women. In this elderly group, body mass index kg/m$^2$) and $E_1$, but not androgens were related to bone mass. Within each race, bone mass increased linearly with increasing concentrations of serum $E_1$ (Cauley, et al., 1994). Furthermore, the levels of free testosterone(fT), but not total T, in older white women relate to the bone density of the spine, hip, and wrist (Greendale, et al., 1995). Thus, depending on age, the levels of the biologically active fT may correlate better with bone mass.

In an earlier study, trabecular bone density correlated significantly only with serum A in women ranging in age from 21 to 48 years (Buchanan, et al., 1988). Among women with normal serum androgen levels, cortical bone density correlated with serum total T and biologically active fT. In theory, this increased cortical mass should help prevent fractures later in life. Endogenous androgens have an anabolic effect on bone density and trabecular density (spine) was significantly increased in the women with androgen excess (Buchanan, et al., 1988). A correlation was found between sex hormone-binding globulin (SHBG), dihydroepiandrosterone sulfate (DHEAS), androgens, and bone mass in premenopausal women (Johnston, et al., 1993). Free testosterone was the androgen most consistently correlated with bone mass at all measured sites. Therefore, it seems clear that androgens are related to bone mass in premenopausal women.

d) Evidence of Oral Contraceptive Effects on Bone of Premenopausal Monkeys and Women In order to determine the effect of oral contraceptive therapy on bone density and serum markers of bone metabolism, a prospective, longitudinal study of young adult female cynomolgus monkeys was undertaken by the present inventors. Two hundred and seven intact monkeys were divided into two groups, and fed an atherogenic diet containing either no drug (Control) or a triphasic oral contraceptive regimen (Triphasil®).

Pre-treatment and periodic post-treatment measurements of bone density and serum bone biomarkers were performed. No significant differences in pre-treatment variables were observed. Both groups of animals gained bone mineral density (BMD) during the study, indicating that they had not yet reached their peak bone mass. Triphasil®-treated animals gained less lumbar spine bone mineral over the course of the study than control animals, resulting in a lumbar spinal bone mineral density which became significantly different from controls by 20 months. Repeated measures analysis of longitudinal data demonstrated that whole body bone mineral content (BMC) as well as spinal BMC and density were significantly lower in Triphasil®-treated animals compared to untreated intact controls at 10 and 20 months of treatment.

Serum alkaline phosphatase (ALP) levels were markedly reduced in the Triphasil® group, while serum acid phosphatase (ACP) and calcium were reduced to a lesser extent. The results suggest that triphasic oral contraceptive treatment of young adult female monkeys that have not reached peak bone mass inhibits net bone accretion by reducing the rate of bone turnover, an effect which may result in a lower peak bone mass in these animals.

One mechanism to account for these findings is that the balance of bone resorption and bone formation has been altered such that formation is less than resorption. Indeed, oral contraceptive treatment caused a 40% reduction in a marker of bone formation (serum ALP) while causing much smaller changes in resorption markers (10–15% reduction in ACP and only minimal effects on TRAP). Thus, oral contraceptive therapy may reduce bone formation more than bone resorption, such that net bone accretion in these young animals is lessened compared to untreated cycling females.

An additional explanation relates to the idea that there is an optimum window for bone turnover rate above or below which bone will not be sufficiently maintained. Ovariectomy of cynomolgus monkeys results in an elevated bone turnover rate. Like women, treatment of ovariectomized animals with estrogen replacement therapy either with or without medroxyprogesterone acetate results in decreased markers of bone resorption and formation along with increased spinal BMC and BMD compared to untreated controls.

The inventors' oral contraceptive study suggests that decreases in bone turnover in young monkeys before peak bone mass also parallels reductions in bone mineral accretion under different circumstances. Perimenopausal and postmenopausal women may experience bone loss which coincides with an increased bone turnover rate, and estrogen replacement therapy can inhibit this bone loss by reducing bone turnover rate.

In perimenopausal women receiving oral contraceptives, although serum osteocalcin (bone gla protein [BGP]) did not change, urinary excretion of hydroxyproline decreased and paralleled a significant (p<0.001) increase in vertebral BMD (Gambacciani, et al., 1994). However, in healthy premenopausal adolescent women and animals, reductions in bone turnover rate may be accompanied by a reduced net bone mineral accretion compared to the normal state, leading ultimately to lower peak bone mass.

In a one-year prospective study, the effects of an oral contraceptive containing 20 $\mu$g ethinyl estradiol plus 0.150 mg desogestrel on bone metabolism were studied in 19 women aged 20 to 30 years. Bone density showed a slight but not significant increase at the end of the trial. Both urinary hydroxyproline-to-creatinine ratio and serum ALP levels showed a significant decrease. The results suggest that bone resorption was reduced, although bone density in the distal radius was not significantly increased in young women using oral contraceptives (Mais, et al., 1993).

The mean age of the animals at the initiation of this present study was estimated through dentition to be 6 years. This is about the time of growth plate closure in this species, but before the attainment of peak bone mass at 9 years (Jayo, et al., 1994). Although women are sexually mature in their early teens, skeletal maturity as reflected by peak bone mass is not reached until about 30 years of age (Recker, et al., 1992). In terms of skeletal maturation, these monkeys may correspond to women between 15 and 30 years of age. Thus, the results may be indicative of oral contraceptive effects on nearly mature skeletons, not in situations where peak bone mass has already been attained. However, the relationship between depression of bone turnover and bone mineral accretion does not appear to be solely due to the fact that the animals are still growing, because trunk length measures did not change significantly between treatment groups.

Pharmacological Compositions

It is understood that the pills formulated according to the present invention may contain ingredients to serve as fillers, binders and for color coding purposes. These ingredients are in common use in present oral contraceptive formulations and may include, but are not limited to, lactose, corn starch, calcium phosphate, povidone, magnesium stearate, stearic acid, colloidal silicon dioxide, hydroxypropyl methylcellulose, polyethylene glycol and one or more of the following dyes: FD&C Blue No. 1 Lake, FD&C Blue No.2 Aluminum Lake, D&C Green No. 5, D&C Yellow No. 10, FD&C Yellow No. 6 or FD & C Red No. 3. Of course these are only exemplary fillers and dyes, those of skill in the art will recognize that other inactive ingredients may be used in the preparation of the formulations of the present invention.

Androgenic side effects may be experienced at the higher doses. Early side effects that are easily recognized and detected by the patient and physician include acne and hirsutism, both of which imply that dose reduction should be considered. These symptoms are readily reversible if detected early. Advanced hirsutism, voice changes, changes in muscle mass etc. are more advanced androgen excess side effects that are avoidable by response to early detection and adjustment of dosages accordingly. In order to minimize side effects it is suggested that a minimal effective dose for beneficial action on bone mass accrual is in the range of 1.25 mg/day. However it is understood that individual cases may require a greater or lesser dose as deemed necessary by the practitioner.

Any of the formulations presented herein may be supplied in a dispenser designed for a one month supply. A typical dispenser would provide for 28 pills to be taken one a day in a determined order. Exemplary dispensers are those described in U.S. Pat. No. 4,165,709, U.S. Pat. No. 4,807, 757, U.S. Pat. No. 3,678,884 or U.S. Pat. No. 3,651,927 (each incorporated herein by reference). It is understood that the dispenser or dispensing means, in and of itself, does not constitute the present invention, and any dispenser means that separates the pills into individual packages and provides a means to dispense the pills one at a time in a particular order so that the user would know which pill to take on any particular day would be acceptable. One or more monthly dispensers may also be contained in a box, such as a cardboard box, for example, that also may contain product information and or instructions for use. The dispensers may also be contained in a decorative type of box that is not immediately identifiable as a birth control pill dispenser.

Methodology for Animal Studies

Female cynomolgus monkeys provide a good animal model for examination of hormone effects on bone metabolism. Monkeys have menstrual cycles similar in length and hormonal variations across the cycle to those of women (Mahoney, 1970). In addition, ovariectomized macaques undergo bone changes that respond to estrogen replacement therapy in ways similar to those observed in postmenopausal women (Jerome, et al., 1994). Throughout the trial, bone density, serum and urinary markers of bone turnover, serum sex hormones, plasma lipids, body weight and weight distribution, blood pressure, and bone architecture and morphology were measured. At the end of the trial, all the monkeys were necropsied and the groups compared for bone parameters and coronary artery atherosclerosis (CAA) extent. A prospective trial of this kind cannot be done in human beings because of its invasive nature, expense, and complications from uncontrolled variables.

For the trial, female macaques were divided into 3 groups:

Group 1=Intact, untreated CONTROL

Group 2=Oral contraceptive-treated with Triphasil® p.o., OC

Triphasil® (women's doses): days 1–7, no hormone; days 8 13, 0.03 mg ethinyl estradiol and 0.05 mg levonorgestrel; days 14–18, 0.04 mg ethinyl estradiol and 0.075 mg levonorgestrel; days 19–28, 0.03 mg ethinyl estradiol and 0.125 mg levonorgestrel.

Group 3=Oral contraceptive-treated with Triphasil® plus triphasic methyltestosterone (MT) (Steraloids, Inc., Wilton, N.H.).

Triphasil® +MT (women's doses): days 1–7, no hormone days 8–13, 0.03 mg ethinyl estradiol, 0.05 mg levonorgestrel and 0.40 mg of MT; days 14–18, 0.04 mg ethinyl estradiol, 0.075 mg levonorgestrel, and 0.60 mg of MT; days 19–28, 0.03 mg ethinyl estradiol, 0.125 mg levonorgestrel and 0.40 mg of MT.

Animal Acquisition and Initial Data

One hundred young adult (6 to 8 years old) female cynomolgus monkeys were purchased and imported from Jakarta, Indonesia. The animals were quarantined, as required by law, during which time the experimental diet was given. During the one-month baseline period, in vivo bone densitometry and radiography were used to detect bone abnormalities. Animals with skeletal abnormalities or unclosed epiphyses were replaced. Based on anthropometry (body weight and trunk length), bone densitometry, serum chemistry, and plasma lipid results, the monkeys were assigned to three matched groups (as described above). Group equivalence was verified using baseline data. Twenty-four months after treatment, all animals were necropsied to compare study groups for bone structural and strength changes, and CAA.

Iliac bone biopsies for histomorphometric analysis were collected after fluorochrome labeling at baseline and after 12 months of treatment. Blood and urine were collected at 0, 1, 3, 6, 12, 18, and 24 months. Serum and urine biomarkers of bone turnover were measured at all timepoints. Lumbar spine, hip and whole monkey were measured at 0, 6, 12, and 24 months. Blood lipids measured at 0, 6, 12, 18, and 24 months and LDL molecular weight determinations were performed at month 12. Body measurements (body weight, trunk length, etc.) were taken every six months (at DEXA scan times).

Statistical power calculations (Dupont and Plummer, 1990) were done to determine minimum sample size to detect anticipated differences in means between any two groups. Estimates of variability in bone mineral density (BMD), bone structure evaluated by histomorphometry (Bone volume/total volume % [CnBV %]), serum markers of bone metabolism (alkaline phosphatase, ALP), and CAA intimal areas were calculated from current studies. Table 3 below lists the adjusted group size (n), detectable difference, power, and two-sided level of significance for primary endpoints.

TABLE 3

Primary Endpoint Data

| Variable | Detectable Difference | Group (n) | Power ($\beta$) | 2-sided ($\alpha$) |
|---|---|---|---|---|
| BMD | 4% | 30 | 0.80 | 0.05 |
| CnBV % | 33% | 19 | 0.80 | 0.05 |
| ALP | 23% | 24 | 0.80 | 0.05 |
| CAA | 70% | 30 | 0.75 | 0.05 |

Allowing for a 5% annual mortality rate (based on a present study and after 24 months of treatment; 67 alive from 75 original monkeys), 100 monkeys were randomized into three treatment groups to obtain 90 evaluable animals after two years of treatment. The inventors targeted detectable differences that appear to be clinically relevant, biologically plausible based on endpoints in studies cited above in Table 3, and reasonable based on the inventors findings in a recent thiazide study (Jayo et al., 1995).

Maintenance and Diet Composition

The monkeys were housed in groups of 4 or 5 monkeys in indoor pens (2.0×3.2×2.5 m) which allow unrestricted mobility and social interaction. Water was provided ad libitum by automatic watering devices. Monkeys were fed a moderately atherogenic semi-purified diet. The diet contained 43% of calories from fat and 0.30 mg of cholesterol/ Cal. This diet is generally expected to induce total plasma cholesterol concentrations of about 200–400 mg/dl. The diet contains 2.5 IU of vitamin $D_3$/g of diet with a calcium (Ca) to phosphorus (P) ratio of 1.0 (207 mg Ca and 206 mg P per 100 g diet). The vitamin $D_3$ amount and Ca/P ratio are appropriate for this species. The diet has been used previously at the CMCRC (Jayo, et al., 1995). Guidelines established by institutional Animal Care and Use Committee, state and Federal laws, and standards of the Department of Health and Human Services were followed throughout the study.

Triphasil® (ethinyl estradiol [EE] and levonorgestrel [LNG]) were added to this diet composition for Group 2, and Triphasil® plus MT were added to this diet for Group 3. The appropriate drug doses were added to the diet and fed on the prescribed days of the month as described above. The Control group (Group 1) were fed the basic diet without added hormones through the 28-day cycle.

Screening and Sampling

Immediately following the quarantine period, the monkeys entered a 30-day baseline period. During this month, blood and urine were collected for analysis of markers of bone turnover, plasma lipids, and hormone determinations. Animals were sedated (ketamine hydrochloride, 15 mg/kg i.m.) for blood and urine collection. Normal ovarian function of the monkeys was determined by following menstrual cycles during quarantine, and by vaginal swabs thereafter. Radiographs were taken for vertebral size, deformity score and pathologic screening. BMC and BMD were measured by DEXA. Body measurements, including BW, trunk length, skinfolds, and trunk and appendicular circumferences were measured. After these determinations, the animals were assigned into three study groups with comparable bone mineral status, anthropometric measurements, serum bone biomarkers, and lipid profiles.

Treatments

Control intact monkeys received no medication mixed in their food. Group 2 animals consisted of intact monkeys given Triphasil® (Wyeth-Ayerst, a triphasic oral contraceptive) for 24 months. Group 3 monkeys were intact given Triphasil®+triphasic methyltestosterone for 24 months. An oral delivery system was selected because this is the route used by women and because the liver may affect drug metabolism. Animals were monitored closely for clinical signs of disease, and if needed, supplements were given in the diet to all groups. A triphasic methyltestosterone formulation was selected based on the normal rhythmic levels of hormone (testosterone/ethinyl estradiol ratio) observed through the female monkey estrous cycle (Wilson, et al., 1982). The doses of MT selected were to provide for an androgenic stimulus similar to T during the estrous cycle. Higher doses present in drug formulations available for postmenopausal women (Estratest®, Solvay Pharmaceuticals, Marietta, Ga.) may cause unwanted side effects in premenopausal adolescent women (Hickock, et al., 1993; Watts, et al., 1995).

General Health Profile

Upon arrival at the center, an initial physical examination provided information on each animal's health and conditioning. If needed, hematological and clinical chemistry parameters were measured, including complete blood counts and differentials, total serum protein, albumin, serum glucose, urea, nitrogen, creatinine, calcium and phosphate. Urinalysis and fecal samples were tested as needed. A set of normal reference values for female cynomolgus macaques were established. Complete blood counts were done on an automated cell counter (Coulter Counter $M_4$30, Hialeah, Fla.), and leukocyte differentials were also performed. CBCs, liver function tests, total serum protein levels, and glucose were measured throughout the study period.

Body Measurements

Body weight (kg) and trunk length (TL, cm) from suprasternal notch to pubic symphysis were used to calculate body mass index (BMI=BW/[TL/100]$^2$). Thickness (mm) of triceps, subscapular, suprailiac, abdominal, mid-thigh, midscapular, and chest skinfolds were measured. Also, circumference (cm) of waist, hip, thigh, and upper arm were measured (Shively, et al., 1987).

Bone Densitometry

Measurements of bone mineral content and density of lumbar vertebrae (L2–L4), whole monkey, and hip were done in vivo under intramuscular ketamine hydrochloride (15 mg/kg i.m.) and acepromazine maleate (0.15 mg/kg i.m.) anesthesia using procedures previously described (Jayo, et al., 1991). Bone density provides a basis for group assignment and permits comparison of results with similar data from human clinical trials. DEXA scans were taken at baseline and at 6, 12, 18, and 24 months.

Serum and Urine Bone Biomarkers

It is difficult to obtain true and multiple dynamic measurements of bone turnover, especially of resorption, by histomorphometry. Serum and urine biomarkers provide the only economical and practical way to measure formation and resorption without invasive surgery. Serum and urine bone biomarkers were assayed at baseline and at 1, 3, 6, 12, 18, and 24 months. Serum total ALP (bone formation), ACP and tartrate-resistant ACP (TRAP, bone resorption), calcium, and phosphorus were measured using a Cobas Fara Chemistry Analyzer (Roche Diagnostics, Nutley, N.J.) (Carlson, et al., 1992; Jayo et al., 1995; Jerome, et al., 1994). Serum BGP (bone turnover) assays were performed using an established radioimmunoassay. Bone resorption was measured using FDA-approved N-telopeptide collagen excretion markers (Osteomark®, Ostex, Seattle, Wash.). Type I collagen cross-linked N-telopeptides in postmenopausal women are reduced to levels seen in premenopausal women by six weeks of estrogen replacement therapy (Hanson, et al., 1992).

Hormonal Assays

Plasma concentrations of testosterone, free testosterone, methyltestosterone, estrone, estradiol, ethinyl estradiol, sex hormone-binding globulin, and androstenedione were measured by established procedures at the Yerkes Regional Primate Research Center's assay laboratory. MT was measured to test efficacy of delivery system and conversion (if any) to T.

Plasma Lipids

Total plasma cholesterol, triglyceride, and HDL cholesterol analyses (Jayo et al., 1994) were performed by enzymatic techniques using a Cobas Fara Chemistry Analyzer (Roche Diagnostics, Nutley, N.J.). LDL molecular weight and fractionation was also measured.

Blood Pressure Measurements and Electrocardiograms

Blood pressure was measured while the animals were sedated. The animals were laid on their right side, and the right arm was extended in a cephalad direction until the upper arm was approximately perpendicular to the vertical axis of the body. The upper arm circumference was measured midway between the shoulder and the elbow, and an appropriate size cuff was used. Three measurements of systolic blood pressure, diastolic blood pressure, and heart rate were taken (Castro, et al., 1981). The average of these measurements was recorded. Blood pressure was measured with a Dinamap Portable Adult/Pediatric and Neonatal Vital signs Monitor (Model 8100) which uses an oscillometric technique to measure systolic, diastolic, and mean arterial pressures and heart rates non-invasively. This device computes pressures and rates, eliminating subjective interpretation (Corbett, et al., 1981). A Medica Systems (Greendale, N.Y.) Cardiomatic electrocardiograph (Model MSC20001) was used for cardiologic evaluations. Electrocardiograms were taken with the animal placed in dorsal recumbency, and the standard leads (I, II, III, AVR, AVL, AVF) and three chest leads V-1,V-4,V-6) were recorded.

Bone Collection and Processing for Histomorphometry

Fluorochrome Labeling

Bone histomorphometry requires prior in vivo administration of bone-seeking fluorochrome labels. Monkeys were given sterile intravenous injections on day 1, followed by 14 days of rest and a second labeling injection given on day 21. Seven to 10 days later, a biopsy or necropsy sample was taken. One of the following bone-seeking fluorochromes was used in all monkeys at each of the three bone collection time points: calcein (10 mg/kg), xylenol orange (90 mg/kg), or demeclocycline hydrochloride (20 mg/kg) of course these are only example of fluorochromes and those of skill in the art may employ other fluorochromes.

This type of application allows for dynamic parameters to be measured (Jerome, et al., 1994, Carlson, et al., 1992). Some differences in measured bone formation rates may occur at different timepoints due to differences in incorporation rates of these labels (Goodwin and Jerome, 1987). By giving the same fluorochrome at each time point there is a reduction in the variability for between-group comparisons at a single time point, but the possible variation in label incorporation is taken into account in analysis of change through time. Measurement of the distance between and extent of labels permits calculation of bone formation rates, while the use of different fluorochrome labels permits the recognition of prior bone mineralization activity.

Iliac Biopsy

Two iliac crest biopsies were collected from each animal, one from each side. Based on available data (Table 10), ovariectomized animals have approximately twice the cancellous bone turnover rate of hormone replaced animals, resulting in replacement of 50–100% of iliac crest cancellous bone each year. Histomorphometric analysis of iliac biopsies taken at one-year intervals enables characterization of functional changes in cancellous bone, since most of the bone present had been formed during the one-year interval. Left iliac crest biopsies were collected aseptically at baseline and from the right ileum one year after initiation of treatment. The method developed by the inventors for iliac bone biopsy in monkeys provides cortical and cancellous bone, with adequate bone area and perimeter for analysis (Goodwin and Jerome, 1987).

Bone Histologic Processing

Histomorphometry: Iliac biopsies and necropsy bone specimens for histomorphometric analysis were fixed in 70% ethanol, processed, embedded in methyl methacrylate/ dibutyl phthalate, and sectioned by one or both of the following methods: 1) Sectioned with a LKB Macrotome sledge microtome or a Jung Supercut rotary microtome at 5–10 $\mu$m, and mounted unstained or stained with alkaline toluidine blue or modified Von Kossa method; or 2) sectioned at 100–125 $\mu$m using an Isomet saw (Buehler, Lake Bluff, Ill.), microradiographed in a Faxitron cabinet (Hewlett-Packard, Rockville, Md.), and/or stuck to glass slides, polished, and surface stained by von Kossa methodology.

Immunocytochemistry: Selected necropsy specimens were fixed in freshly prepared cold 4% paraformaldehyde to maintain antigenic properties and processed in one or both of the following two methods: 1) embedded in methylmethacrylate, undecalcified or 2) decalcified in 1% EDTA, paraffin embedded, and serially sectioned for immunocytochemical or in situ hybridization studies. The inventors have developed reliable techniques that enable the evaluation of the presence and/or production of bone-related proteins (Tulli, et al., 1992; Carlson, et al., 1993).

Standard Histomorphometry of Multiple Bone Envelopes

The present study uses modification of methods described by Parfitt, et al. (1987a). The measurements and abbreviations used were based on the ASBMR standard nomenclature (Parfitt, et al., 1987b). Structural and dynamic parameters were derived separately for periosteal (Ps), haversian (H), endocortical (Ec), and cancellous (Cn) bone envelopes. Bone volume was also calculated for H+Ec and for all (Tt) envelopes combined. This analysis is primarily of value for analysis of dynamic (functional) changes in bone, enabling assessment of the relative contributions of the cortical-endosteal and cancellous envelopes to bone macro- and microarchitectural changes. Using this method, it is possible to determine the relative contributions of the different envelopes to structural change resulting from experimental manipulation. Additional parameters which may be included in this analysis are measurement of erosion depth and wall thickness to determine bone balance per remodeling cycle and activation frequency (Cohen-Solal, et al., 1991). This analysis is time consuming, and even with the assistance of automated methods, is only be feasible on one section per bone.

Automated Histomorphometric Analysis of Multiple Bone Sections

Multiple cross-sections of femur neck, femur diaphysis, lumbar vertebra, and distal radius were cut with an Isomet saw, surface-stained and/or microradiographed, and analyzed using an Apple Power PC with NIH Image Analysis System. Microradiographed or von Kossa-stained sections have sufficiently high contrast that bone and marrow can be readily distinguished by thresholding of gray-scale images obtained with a color camera. The thresholded gray-scale images are converted to binary bit-maps (which may be represented as black and white images), from which measurements can be extracted rapidly.

Necropsies and Tissue Collection

After the 24-month DEXA scan, the animals were further sedated with ketamine hydrochloride (10 mg/kg body weight) for transport to the necropsy laboratory. Sodium pentobarbital (13 mg/kg body weight) was administered intravenously to attain surgical anesthesia. An infusion of Ringer's solution is initiated via an 18 gauge needle inserted into the left ventricle. Euthanasia was effected with a 5 ml (325 mg) intravenous injection of sodium pentobarbital. A 1 cm longitudinal incision made in the abdominal inferior vena cava allowed drainage of blood from the cardiovascular system. The heart and major vessels were dissected out and prepared for perfusion with 10% neutral buffered formalin (NBF) at a pressure of 100 mm/Hg for 1 hour. The heart, aorta and carotid and iliac arteries were carefully dissected free and immersion fixed in 10% NBF until further preparation. The brains, including the intracranial arteries, were removed and immersion fixed in 20% NBF. All major organ systems were examined grossly. Reproductive, endocrine, cardiovascular, and other soft tissues were collected, fixed in 4% paraformaldehyde and/or snap frozen with liquid nitrogen, and carefully evaluated for changes due to treatment.

After the soft tissues were removed from the carcass, both femoral heads are ex vivo scanned by DEXA at a high resolution to describe regional differences in BMC, including the femoral neck, Ward's triangle, and mid-diaphysis (cortical bone). Both humeri, the right femur, and the lumbar 3 & 4 vertebrae as a pair were wrapped in wet (Ringer's or saline) gauze, identified with a tag, and placed in properly labeled Ziploc® bags to be frozen at −20° C. and used as needed for further study.

The left radius and lumbar 2 and 5, and thoracic vertebrae 6 through 9 were fixed in 70% ethanol for histomorphometric analysis. The left femur was placed in 10% NBF for DEXA scan and then transferred to 70% ethanol. Both knees were fixed in 10% NBF and later in 70% ethanol for arthritis evaluation of articular cartilage and subchondral bone. Sternebrae and thoracic vertebra 13 were sectioned longitudinally (1 to 3 mm thick) with the Isomet saw (after removal of dorsal arches and transverse processes), and fixed in cold 4% paraformaldehyde. After 24 hours, these sections were transferred to 40% ethanol. The slabs were processed for immunocytochemistry (Tulli, et al., 1992) and in situ hybridization.

Biomechanical Testing

Frozen bones were submitted for biomechanical fracture tests and bone strength analyses. Mechanical testing includes shear tests on the femoral necks, three-point bending of humerus mid-diaphysis, and fatigue testing on vertebrae.

Coronary Artery Atherosclerosis Evaluation

To study the extent and severity of coronary artery atherosclerosis, 15 blocks (each 3 mm in length) cut perpendicularly to the long axis of the arteries were taken. Five of these were serial blocks from the left circumflex, five from the left anterior descending, and five from the right coronary artery. The tissue blocks were dehydrated through increasing concentrations of ethanol and embedded in paraffin. Two sections (5 $\mu$m) were cut from each block and stained with either hematoxylin and eosin or Verhoeff-van Gieson's stain and morphometrically evaluated. Verhoeff-van Gieson's stained sections of arteries were projected, using a projection microscope, onto a digitizer plate. Using a hand-held stylus and a computer-assisted digitizer, the component parts of the artery were traced.

Measurements of the intimal area, intimal area per unit length of internal elastic lamina, area within the internal elastic lamina, and coronary artery luminal area were taken. Intimal areas were determined by digitizing the area between the internal elastic lamina and the luminal surface of each coronary artery section. An integration method was used for calculations of intimal areas. The area of the intima describes plaque size. To obtain the intimal area per unit length of internal elastic lamina, the length of the internal elastic lamina was divided into the intimal area. This measurement provides information about the average intimal thickness for a given section of coronary artery. The length of the internal elastic lamina (circumference) was used to calculate the area. This measurement characterizes artery size. The area within the external elastic lamina could be measured, but the interpretation of its precise location is less clear than that of the internal elastic lamina. The two measurements were correlated highly, hence internal elastic lamina was used as a measure of size.

Soft Tissue Evaluation

Formalin-fixed, paraffin-embedded, and hematoxylin and eosin stained sections of all other soft tissues were evaluated.

Data Analysis and Interpretation

Statistical Methods

Values obtained by sequential sampling, such as histomorphometry, densitometry, and serum and urine chemistry measurements, were analyzed using repeated measures analysis of variance (ANOVA) or covariance (ANCOVA) or by appropriate nonparametric methods. Where comparisons of any two data points were of interest, appropriate parametric (t-statistics) or nonparametric (Mann-Whitney or Wilcoxon) tests were used. Regression and correlation models (parametric and nonparametric) were used to examine the relationships between variables; for example, the correlation between histomorphometric and absorptiometric measures. Linear and curvilinear regression analyses were used to examine rates of change over time. All parametric analyses presented used the methods of Sokal and Rohlf (1981), and nonparametric analyses used the methods of Seigel (1956).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Oral Contraceptive Effects on Bone Metabolism in Primates

Animals

Two-hundred and seven female cynomolgus monkeys (*Macaca fascicularis*) were part of a comparative clinical trial designed to determine if the premenopausal use of a contraceptive steroid (Triphasil®) influenced the progression of CAA and osteoporosis after surgical menopause. The average age (estimated by dentition) of the animals was approximately 6 years, and was not significantly different between groups (p>0.40). The 207 animals were randomized to one of two treatment groups of 103 untreated animals (Control) and 104 oral contraceptive (Triphasil®)-treated animals. The data presented here were transformed when necessary to reduce skewness and equalize group variances, and subjected to analysis of variance (ANOVA) or repeated measures analysis of covariance (ANCOVA). All data presented represent the mean ±SEM of the untransformed data. Longitudinal bone densitometry data from 0, 10 and 20 months were analyzed by repeated measures ANCOVA. Data from 0 months (baseline) were used to control for pre-treatment variation.

Drug Administration: Female cynomolgus monkeys consume approximately 17% of the calories (dose) of the average woman, or about 306 calories/day. Oral contraceptive dosage was calculated to approximate the human dose based on an estimated caloric intake of 120 calories/kg body weight (or 1800 calories/day for an average adult woman) and given mixed in the diet. Therefore, the Triphasil®-treated monkeys were fed four separate diet formulations (days 1–7, no hormone; days 8–13, 0.03 mg ethinyl estradiol and 0.05 mg levonorgestrel; days 14–18, 0.04 mg ethinyl estradiol and 0.075 mg levonorgestrel; days 19–28, 0.03 mg ethinyl estradiol and 0.125 mg levonorgestrel).

The diets contained 0.55 IU Vitamin $D_3$/calorie (168 IU/day), 1.75 mg calcium/calorie (535 mg/day), and 1.49 mg phosphorus/calorie (456 mg/day) for a calcium/phosphorus ratio of 1.17. This level of calcium intake translates to 3147 mg calcium/day for a woman consuming 1800 calories/day, which is >3 times the calcium intake (1000 mg/day) recommended for young women (see Kanders, et al., 1988), and is more than twice the recommended calcium intake of 1500 mg/day for postmenopausal women. The dietary vitamin $D_3$ levels correspond to about twice the recommended daily dose in women.

Bone Densitometry: Lumbar spine (L2–L4) bone mineral content (BMCsp, g) and density (BMDsp, $g/cm^2$), and whole body bone mineral content (BMCw, g) were measured with a Norland XR26 dual-energy X-ray absorptiometer (DEXA; Norland, Ft. Atkinson, Wis.). Two hundred and seven animals were scanned once at time 0 and after 10 months of treatment, of these 188 were also scanned after 20 months of treatment. BMCsp was not significantly different between groups at any timepoint. BMDsp was not significantly different between groups at time 0, but became significantly lower (p<0.05) in the Triphasil® group at 10 months, and remained significantly lower after 20 months of treatment. While BMCsp and BMDsp both increased with time, there were significant group X time interactions, indicating that the treatment groups were changing differently over time.

Triphasil® animals had smaller increases in BMCsp and BMDsp over time compared to untreated Controls. BMCw also increased with time in both groups, and there was also a significant group X time interaction. Triphasil® animals gained less BMCw than Controls after 10 months of treatment.

Serum Biomarkers: Serum was collected prior to treatment and at regular 5-month intervals during treatment for assessment of circulating markers of bone metabolism. Sampling was carried out on day 21 of the hormonal regimen. Serum ALP (U/L), ACP (U/L), TRAP (U/L), calcium ($Ca^{2+}$, mg/dl, and inorganic phosphate (Pi, mg/dl) were determined using a Cobas Fara 11 autoanalyzer employing protocols and reagents supplied by Roche Diagnostic Systems, Inc. (Nutley, N.J.). Serum ALP levels were decreased by about 43% compared to the baseline values in the Triphasil® group, while decreasing only slightly (12%) in the Control group compared to baseline values. During the course of the study, the serum ALP activity in Triphasil®-treated animals was approximately 55–60% of that in the control group. Serum ACP and $Ca^{2+}$ also were significantly lower in the Triphasil® animals, while no significant treatment effect was observed on TRAP, but cyclical effects were seen in the serum Pi levels. Consequently, the Triphasil® group had reduced serum markers of bone resorption (ACP) and bone formation (ALP).

Serum androgen levels: Oral contraceptive use causes a time-dependent suppression of serum DHEAS by 20–30% (p<0.01) and A, and a significant decrease in levels of total T by 30–35% (p<0.01) and fT by 60% (p<0.01), while SHBG was increased by 200–240% on days 11 and 21 (p<0.01). The results demonstrate a profound suppression of androgen levels and peripheral androgen metabolism (Wiegratz, et al., 1995; Kuhn, et al., 1994).

In the monkey study, serum was collected at 10 and 20 months and total T, A, and DHEAS measured. As shown in Table 4, the Triphasil® group had approximately half the serum levels of androgens than the Control group.

TABLE 4

Serum androgen concentrations in premenopausal monkeys
(mean ± SEM).

|  | Control | Triphasil ® | p-value |
|---|---|---|---|
| T (ng/ml) | 0.367 ± 0.019 | 0.182 ± 0.009 | 0.0001 |
| A (ng/ml) | 3.96 ± 0.191 | 1.89 ± 0.092 | 0.0001 |
| DHEAS (µg/ml) | 15.43 ± 1.06 | 12.09 ± 0.86 | 0.015 |

Anthropometric and Densitometric Measurements

Anthropometic and densitometric measures (means±sem) for the two treatment groups at the various timepoints are presented in Table 5. As denoted in Table 5, the number of observations per group decreased over time in the study, as densitometry data was available for 207 animals at the 0 and 10 month timepoints and 188 animals at the 20 months timepoint. For this reason, each timepoint was initially analyzed separately. Body weight, trunk length, BMCw, and BMCs were not significantly different between groups at any timepoint. BMDs was not significantly different between groups at time 0, but became significantly lower in the Contraceptive group at 10 months, and remained significantly lower after 20 months of treatment.

Since the number of observations decreased by the third timepoint (20 months), the data were analyzed by a 2×2 analysis of variance for the 0 and 10 month data. In order to examine long term effects, the data were analyzed by 2×3 ANOVA of all three timepoints or a 2×2 ANCOVA of the 10 and 20 month measurements adjusted for pretreatment measures.

TABLE 5

Analysis of variance for individual timepoint comparisons of anthropometric and densitometric data for 207 intact female cynomolgus macaques at 0 and 10 months and 188 animals at 20 months taking placebo (CONTROL) or contraceptives (CONTRACEPTIVE) and analyses of variance (ANOVA).
Values are means ± s.e

|  | CONTROL | CONTRACEPTIVE | n | p |
|---|---|---|---|---|
| Body Weight (kg) | | | | |
| 0 months | 2.80 ± 0.04 | 2.89 ± 0.04 | 207 | 0.15 |
| 10 months | 2.89 ± 0.04 | 2.97 ± 0.04 | 207 | 0.20 |
| 20 months | 2.89 ± 0.04 | 2.99 ± 0.04 | 188 | 0.08 |
| Trunk Length (cm) | | | | |
| 0 months | 26.9 ± 0.01 | 27.0 ± 0.01 | 207 | 0.59 |
| 10 months | 27.0 ± 0.01 | 27.1 ± 0.01 | 207 | 0.42 |
| 20 months | 27.0 ± 0.01 | 27.2 ± 0.01 | 188 | 0.23 |
| BMC-Spine L2-4 (g) | | | | |
| 0 months | 4.23 ± 0.08 | 4.27 ± 0.07 | 207 | 0.73 |
| 10 months | 4.54 ± 0.08 | 4.46 ± 0.08 | 207 | 0.46 |
| 20 months | 4.63 ± 0.09 | 4.50 ± 0.08 | 188 | 0.30 |
| BMC-Spine L2-4 (g/cm2) | | | | |
| 0 months | 0.476 ± 0.006 | 0.473 ± 0.005 | 207 | 0.65 |
| 10 months | 0.507 ± 0.006 | 0.490 ± 0.006 | 207 | 0.04 |
| 20 months | 0.515 ± 0.006 | 0.494 ± 0.006 | 188 | 0.02 |
| BMC Whole Body (g) | | | | |
| 0 months | 111.5 ± 2.1 | 114.1 ± 2.0 | 207 | 0.78 |
| 10 months | 122.3 ± 2.2 | 122.6 ± 2.0 | 207 | 0.91 |
| 20 months | 123.8 ± 2.5 | 122.7 ± 2.0 | 188 | 0.72 |

The results from repeated measures ANOVA at 0 and 10 months for these variables are presented in Table 6. Body weight, which was not different between groups at baseline, increased significantly in both groups with time on diet. No group or time effects were found for trunk length over the first 10 months. While spinal (L2–4) BMC and BMD both increased with time, there were significant group×time interactions, indicating that the treatment groups were changing differently over time. Oral contraceptive treated animals had smaller increases in spinal BMC and BMD over time compared to untreated controls. Whole body BMC also increased with time in both groups, and there was also a significant group×time interaction. Contraceptive-treated animals gained less BMC than controls after 10 months of treatment.

TABLE 6

Repeated measures analysis of variance for anthropometric and densitometric measurements of 207 intact female cynomolgus macaques taking placebo (CONTROL or contraceptives (CONTRACEPTIVES) at 0 months (baseline) and after 10 months of treatment.

|  |  | p |
|---|---|---|
| BODY WEIGHT (kg) | group | 0.168 |
|  | time | 0.000 |
|  | group × time interaction | 0.792 |
| TRUNK LENGTH (cm) | group | 0.493 |
|  | time | 0.113 |
|  | group × time interaction | 0.402 |
| BMC-SPINE L2-4 (g) | group | 0.831 |
|  | time | 0.000 |
|  | group × time interaction | 0.001 |
| BMD-SPINE L2-4 (g/cm$^2$) | group | 0.201 |
|  | time | 0.000 |
|  | group × time interaction | 0.000 |
| BMC-WHOLE BODY (g) | group | 0.621 |
|  | time | 0.000 |
|  | group × time interaction | 0.025 |

Longitudinal anthropometric and bone densitometry data from 0, 10 and 20 months was analyzed by repeated measures ANCOVA. Data from 0 months (baseline) was used to control for pretreatment variation. Individual means and standard deviations of the data from animals receiving evaluations at all three timepoints are presented, along with ANCOVA statistics and adjusted cell means (Tables 7 and 8). Values vary slightly from that presented in Table 5 due to the elimination of incomplete data. Body weight, which significantly increased over the first 10 months, did not change over the second 10 month period and showed no group or group×time interactions (Table 7). Trunk length increased over time as evidenced by a very slight increase in both groups, although no group or group×time interactions were observed.

TABLE 7

Repeated measures analysis of variance[1] and covariance[2] for the complete anthropomorphic data from 0, 10 and 20 month timepoints (group means ± sem).

| BODY WEIGHT (kg) | CONTROL (n = 91) | CONTRACEPTIVE (n = 97) |
|---|---|---|
| 0 MONTHS | 2.80 ± 0.04 | 2.91 ± 0.04 |
| 10 MONTHS | 2.89 ± 0.04 | 3.00 ± 0.04 |
| 20 MONTHS | 2.89 ± 0.04 | 2.99 ± 0.04 |

[1][NO COVARIATE], group p = 0.06; time p = 0.00; group × time interaction p = 0.98
[2][COVARIATE = BW AT 0 MONTHS], group p = 0.75; time p = 0.59; group × time interaction p = 0.92

| TRUNK LENGTH | CONTROL | CONTRACEPTIVE |

TABLE 7-continued

Repeated measures analysis of variance[1] and covariance[2] for the complete anthropomorphic data from 0, 10 and 20 month timepoints (group means ± sem).

| (cm) | (n = 91) | (n = 97) |
|---|---|---|
| 0 MONTHS | 26.9 ± 0.1 | 27.1 ± 0.1 |
| 10 MONTHS | 26.9 ± 0.1 | 27.2 ± 0.1 |
| 20 MONTHS | 27.0 ± 0.1 | 27.2 ± 0.1 |

[1][NO COVARIATE], group p = 0.26; time p = 0.00; group × time interaction p = 0.40
[2][COVARIATE = TL AT 0 MONTHS], group p = 0.17; time p = 0.01; group × time interaction p = 0.86

After adjusting for pretreatment (time 0) differences, significant group, time, and group by time effects were observed for lumbar spinal bone mineral content and density (Table 8). Spinal BMC and BMC increased in both groups between 0 and 10 months, with much smaller increases occurring between 10 and 20 months. Contraceptive-treated animals gained bone at a reduced rate compared to controls, resulting in a lower spinal BMC and BMC at 10 and 20 months of treatment. Significant group, time, and group by time interactions were also observed for whole body BMC. Whole body BMC increased significantly in both Control and in Contraceptive-treated animals over the first 10 months, and increased slightly over the next 10 months in the Control group while decreasing slightly in the Contraceptive group.

TABLE 8

Repeated measures analysis of variance and covariance for complete bone densitometry data from 0, 10 and 20 month timepoints (group means ± sem). Adjusted means for covariate analysis are presented in brackets [ ].

BMC SPINE (g)

| | | |
|---|---|---|
| 0 MONTHS | 4.22 ± 0.08 | 4.29 ± 0.08 |
| 10 MONTHS | 4.52 ± 0.08 [4.56] | 4.48 ± 0.08 [4.45] |
| 20 MONTHS | 4.62 ± 0.09 [4.66] | 4.50 ± 0.08 [4.46] |

[1][NO COVARIATE], group p = 0.78; time p = 0.00; group × time interaction p = 0.00
[2][COVARIATE = BMC(SPINE), TRUNK LENGTH AT 0 MONTHS], group p = 0.00; time p = 0.00; group × time p = 0.00

BMD SPINE (g/cm$^2$)

| | | |
|---|---|---|
| 0 MONTHS | 0.476 ± 0.006 | 0.473 ± 0.006 |
| 10 MONTHS | 0.506 ± 0.006 [0.505] | 0.491 ± 0.006 [0.491] |
| 20 MONTHS | 0.515 ± 0.006 [0.514] | 0.494 ± 0.006 [0.494] |

[1][NO COVARIATE], group p = 0.12; time p = 0.00; group × time interaction p = 0.00
[2][COVARIATE = BMD(SPINE), BMC(SPINE) AT 0 MONTHS], group p = 0.00; time p = 0.00; group × time p = 0.03

| BMC WHOLE BODY (g) | CONTROL (n = 91) | CONTRACEPTIVE (n = 97) |
|---|---|---|
| 0 MONTHS | 111.4 ± 2.0 | 115.0 ± 2.0 |
| 10 MONTHS | 122.0 ± 2.2 [123.8] | 124.0 ± 2.0 [122.4] |
| 20 MONTHS | 123.8 ± 2.4 [125.5] | 122.7 ± 2.0 [121.0] |

[1][NO COVARIATE], group p = 0.61; time p = 0.00; group × time interaction p = 0.00
[2][COVARIATE = BMC(WHOLE BODY), BMC(SPINE) AT 0 MONTHS], group p = 0.00; time p = 0.71; group × time p = 0.00

Bone Biomarkers

Serum biomarker analysis results are presented in Table 9. Since the number of observations changed over time, group comparisons were made for each individual timepoint. Serum alkaline phosphatase levels were decreased by about 43% compared to the pretreatment (time 0) values in the Contraceptive group, while decreasing only slightly (12%) in the control group compared to pretreatment values. During the course of treatment, the serum alkaline phosphatase activity in contraceptive treated animals was approximately 55–60% of that found in the control group. Serum acid phosphatase and calcium were also significantly lower in the Contraceptive group, while no consistent effect was observed on tartrate-resistant acid phosphatase or serum phosphate levels. Thus, the Contraceptive group had reduced serum markers of bone resorption (acid phosphatase) and bone formation (alkaline phosphatase).

TABLE 9

Analysis of variance for individual timepoint comparisons of serum biomarker data.

| | CONTROL | CONTRACEPTIVE | n | p = |
|---|---|---|---|---|
| ALKALINE PHOSPHATASE (U/L) | | | | |
| 0 MONTHS | 197.1 ± 6.8 | 180.2 ± 7.2 | 180 | 0.090 |
| 5 MONTHS | 173.5 ± 6.9 | 103.5 ± 5.9 | 113 | 0.000 |
| 10 MONTHS | 172.7 ± 4.9 | 104.7 ± 3.3 | 174 | 0.000 |
| 15 MONTHS | 190.9 ± 9.1 | 104.8 ± 4.4 | 171 | 0.000 |
| 20 MONTHS | 173.4 ± 9.0 | 102.5 ± 6.8 | 60 | 0.000 |
| ACID PHOSPHATASE (U/L) | | | | |
| 0 MONTHS | 8.39 ± 0.21 | 8.47 ± 0.25 | 180 | 0.820 |
| 5 MONTHS | 8.35 ± 0.31 | 7.89 ± 0.32 | 113 | 0.307 |
| 10 MONTHS | 8.90 ± 0.23 | 7.89 ± 0.17 | 174 | 0.006 |
| 15 MONTHS | 9.01 ± 0.22 | 8.11 ± 0.18 | 172 | 0.002 |
| 20 MONTHS | 8.72 ± 0.35 | 7.07 ± 0.35 | 59 | 0.002 |
| TARTRATE RESISTANT ACID PHOSPHATASE (U/L) | | | | |
| 0 MONTHS | 3.70 ± 0.07 | 3.80 ± 0.06 | 178 | 0.280 |
| 5 MONTHS | 4.12 ± 0.10 | 3.68 ± 0.15 | 113 | 0.013 |
| 10 MONTHS | 4.44 ± 0.09 | 4.33 ± 0.09 | 174 | 0.360 |
| 15 MONTHS | 4.14 ± 0.08 | 4.09 ± 0.10 | 172 | 0.700 |
| 20 MONTHS | 4.35 ± 0.19 | 4.09 ± 0.16 | 59 | 0.306 |
| CALCIUM (mg/dl) | | | | |
| 0 MONTHS | 9.23 ± 0.04 | 9.27 ± 0.04 | 180 | 0.470 |
| 5 MONTHS | 9.12 ± 0.05 | 8.90 ± 0.05 | 113 | 0.005 |
| 10 MONTHS | 9.19 ± 0.07 | 8.96 ± 0.05 | 174 | 0.008 |
| 15 MONTHS | 8.98 ± 0.05 | 8.73 ± 0.04 | 172 | 0.000 |
| 20 MONTHS | 9.03 ± 0.07 | 8.85 ± 0.08 | 60 | 0.092 |
| PHOSPHATE (mg/dl) | | | | |
| 0 MONTHS | 3.78 ± 0.11 | 3.51 ± 0.11 | 180 | 0.079 |
| 5 MONTHS | 3.67 ± 0.08 | 3.99 ± 0.10 | 113 | 0.082 |
| 10 MONTHS | 3.74 ± 0.10 | 3.97 ± 0.09 | 174 | 0.097 |
| 15 MONTHS | 3.71 ± 0.08 | 3.46 ± 0.07 | 172 | 0.015 |
| 20 MONTHS | 3.77 ± 0.14 | 4.00 ± 0.15 | 60 | 0.272 |

The biochemical findings described above suggest that oral contraceptive treatment caused an overall reduction in bone turnover in these animals. Reduction of bone turnover rate is usually associated with preservation of bone mineral, since estrogen replacement therapy appears to preserve bone density in ovariectomized monkeys by reductions in the overall turnover rate. In this case, however, oral contraceptive treatment resulted in reduction of biomarkers of bone turnover along with an apparently negative effect on net bone mineral density relative to Control animals.

These data show that prolonged oral contraceptive treatment reduces net bone accretion and may result in a lower peak bone mass in young female monkeys that are still accruing bone.

EXAMPLE 2

Estrogen Effects on Postmenopausal Monkeys: Bone Histology and Biomechanics

This Example presents the histomorphometric data from studies of postmenopausal monkeys.

Bone Histomorphometry

In untreated ovariectomized women, as in estrogen-deficient ovariectomized monkeys, when bone turnover increases the net effect is bone loss. Previous reports have demonstrated a good correlation between serum markers and histomorphometric data (Jerome, et al., 1994). Studies of the structural changes that occur after ovariectomy in cancellous bone of iliac and lumbar bones of monkeys after 11 months of treatment have been made (Jayo, et al., 1995). Animals were bilaterally ovariectomized and divided into 3 groups: 1) untreated (OVX, 2) receiving estrogen replacement therapy (ERT), and 3) receiving ERT plus thiazide diuretics (ERT+TZ). Table 10 provides iliac cancellous bone histomorphometric information.

TABLE 10

Structural Histomorphometry of Iliac Cancellous Bone in OVX, OVX + ERT, and ERT + TZ Cynomolgus Monkeys (Mean ± SEM, adapted from Jayo, et al., 1995).

| Measurement | OVX (n = 10) | ERT (n = 10) | ERT + TZ (n = 10) | p-value |
|---|---|---|---|---|
| Cancellous bone volume (%) | | | | |
| 0 months | 28.87 ± 2.03 | 27.17 ± 2.97 | 25.47 ± 2.19 | NS |
| 11 months | 17.92 ± 1.51 | 25.65 ± 2.63 | 23.62 ± 1.91 | 0.036 |
| Trabecular thickness ($\mu$m) | | | | |
| 0 months | 130.00 ± 6.27 | 138.05 ± 5.53 | 119.12 ± 7.76 | NS |
| 11 months | 102.12 ± 6.44 | 110.85 ± 7.16 | 101.71 ± 6.29 | NS |
| Trabecular n (/mm) | | | | |
| 0 months | 2.23 ± 0.14 | 1.95 ± 0.18 | 2.14 ± 0.12 | NS |
| 11 months | 1.68 ± 0.14 | 2.23 ± 0.18 | 2.28 ± 0.16 | 0.023 |
| Trabecular separation ($\mu$m) | | | | |
| 0 months | 334.08 ± 28.83 | 412.61 ± 50.08 | 365.54 ± 35.77 | NS |
| 11 months | 540.43 ± 63.10 | 370.66 ± 51.83 | 355.36 ± 29.24 | 0.026 |

Structural changes in midsagittal sections of vertebral cancellous (lumbar) bone 25 months after ovariectomy in monkeys have been documented (Carlson, et al., 1992; Jerome, et al., 1994). There were significant differences in vertebral cancellous bone volume and trabecular thickness, but not in trabecular number or separation between groups (Table 11).

TABLE 11

Structural and Dynamic Histomorphometry of Vertebral Cancellous Bone in Ovariectomized (OVX), OVX + 17-β Estradiol (ERT), and OVX + 17-β Estradiol + Progesterone-treated (ERT + P) Cynomolgus Monkeys (adapted from Jerome, et al, 1994)

| Measurement | OVX (n = 10) | ERT (n = 10 | ERT + P |
|---|---|---|---|
| Cancellous bone volume (%) | 24.3 ± 1.2 | 24.6 ± 1.3 | 8.6 ± 1.02* |
| Osteoid Surface (OS/BS, $\mu$m) | 17.5 ± 3.1 | 6.8 ± 0.9† | 11.9 ± 2.2 |
| Mineral Apposition Rate ($\mu$m/day) | 0.65 ± 0.03 | 0.48 ± 0.02† | 0.56 ± 0.03‡ |

*p < 0.05 vs OVX and ERT
†p < 0.05 vs OVX
‡p < 1.0 vs ERT

In summary, serum biomarker and histomorphometric data indicate that bone formation rate is markedly increased after surgical menopause in monkeys and that bone turnover generally remains elevated for at least 2 years. This functional change is accompanied by architectural changes in cancellous bone and trends toward, and consistent with, a loss of structural elements. In order to test the consequences of having a loss in structural elements, the biomechanical force required to cause a fracture in bone of ovariectomized animals was tested.

Bone Biomechanical Testing

Tibiae collected 30 months after surgery from INT and OVX macaques were collected, frozen, and were tested using an Instron materials testing system (Kasra and Grynpas, 1992). The midshaft was loaded in nondestructive 3-point bending tests to determine modulus of elasticity, followed by destructive torsion tests to determine shear modulus and failure shear stress. Mid-shaft cross-sectional area also was measured. Although cross-sectional area was not different between groups, all other parameters were significantly lower in OVX animals compared to INT animals ($p<0.05$), indicating a postmenopausal weakening of the mechanical properties of the bone and increased fragility (Table 12).

TABLE 12

Mechanical properties of the tibiae of intact (INT) and ovariectomized (OVX) cynmolgus macaques 30 months after surgery (mean ± SD, 2-tailed t-test)

| Test | INT (n = 11) | OVX (n = 11) | p-value |
|---|---|---|---|
| Elastic modulus (MPa) | 9044 ± 400 | 7193 ± 412 | <0.01 |
| Shear modulus (MPa) | 2849 ± 138 | 2215 ± 147 | <0.05 |
| Failure stress (MPa) | 47 ± 2.4 | 35 ± 2.1 | <0.05 |
| Area (mm$^2$) | 37 ± 1.2 | 37 ± 1.5 | NS |

The effects of androgens on the biomechanical properties of bone were evaluated in intact female monkeys (INT), intact monkeys treated with androstenedione plus $E_1$ (ANDRO), and intact monkeys treated with testosterone (TESTO) (Adams, et al., 1995; Kasra and Grynpas, 1995). In this study the TESTO monkeys received supraphysiological levels of T, giving them blood levels of T similar to male monkeys and also a male body composition. Core samples from the femoral head were studied and the results are given in Table 13.

TABLE 13

Mechanical properties of the femoral trabecular bone of INT, ANDRO and TESTO cynomolgus macaques 30 months after treatment (mean ± sd, n = 12 per group)
Adapted from Kasra, et al, 1995
Symbols in common are significantly different (p < 0.05)

| Test | INT | ANDRO | TESTO |
|---|---|---|---|
| Elastic modulus (MPa) | 392 ± 70*† | 737 ± 152† | 812 ± 123* |
| Maximum Stress (MPa) | 23.6 ± 4.8* | 23.2 ± 2.6† | 29.8 ± 5.4*† |
| Density (g/cm$^3$) | 1.326 ± 0.09* | 1.389 ± 0.05 | 1.440 ± 0.06* |

The tibia were also biomechanically tested, and the TESTO group had stronger, tougher, and stiffer tibiae (Kasra and Grynpas, 1995).

These bone studies indicate that skeletal changes in surgically postmenopausal macaques are similar to those that occur in postmenopausal women, including increased bone turnover, decreased bone mass, altered cancellous bone microarchitecture, and compromised bone strength. These changes are prevented by ERT with or without progestins. In premenopausal monkeys, bone strength was increased in androgenized animals, with T-treated animals having stronger and denser bones.

EXAMPLE 3

Atherosclerosis-related Studies in Premenopausal Monkeys

The effects of oral contraceptives on CAA of intact female cynomolgus macaques has been investigated (Clarkson, et al., 1990). In this study young adult female cynomolgus macaques were fed an atherogenic diet and divided into 3 groups: a control group, a group given ethinyl estradiol and norgestrel, and another group given ethinyl estradiol and ethynodiol diacetate. Both contraceptive formulations lowered HDL cholesterol. However, the extent of CAA was lessened by both contraceptives.

The inventors have investigated the effects of experimentally induced hyperandrogenism in female monkeys with diet-induced atherosclerosis (Adams, et al., 1995). After 30 months, CAA was almost twice as extensive $p<0.05$ in TESTO animals relative to untreated INT animals, while ANDRO treatment had no effect on atherosclerosis extent. The atherogenic effects of T were independent of plasma lipoprotein risk variables. Although atherosclerosis extent was greater in TESTO monkeys, vasomotor activity was similar to that of INT monkeys. The inventors have observed that arterial vasomotion of surgical postnenopausal monkeys was not impaired when methyltestosterone (MT) was added to ethinyl estradiol therapy. MT therapy may not suppress the beneficial effects of ethinyl estradiol on the arterial wall.

EXAMPLE 4

An oral contraceptive formulation comprising 28 tablets as follows: 6 tablets containing 0.03 mg ethinyl estradiol, 0.05 mg levonorgestrel and 0.25 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 5

An oral contraceptive formulation comprising 28 tablets as follows: 6 tablets containing 0.03 mg ethinyl estradiol, 0.05 mg levonorgestrel and 0.3 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 6

An oral contraceptive formulation comprising 28 tablets as follows: 6 tablets containing 0.03 mg ethinyl estradiol, 0.05 mg levonorgestrel and 0.5 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 7

An oral contraceptive formulation comprising 28 tablets as follows: 6 tablets containing 0.03 mg ethinyl estradiol, 0.5 mg levonorgestrel and 0.75 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 8

An oral contraceptive formulation comprising 28 tablets as follows: 6 tablets containing 0.03 mg ethinyl estradiol, 0.5 mg levonorgestrel and 1.0 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 9

An oral contraceptive formulation comprising 28 tablets as follows: 6 tablets containing 0.03 mg ethinyl estradiol, 0.5 mg levonorgestrel and 1.5 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 10

An oral contraceptive formulation comprising 28 tablets as follows: 6 tablets containing 0.03 mg ethinyl estradiol, 0.05 mg levonorgestrel and 1.5 mg methyltestosterone to be taken on consecutive days 8–13 of a menstrual cycle; 5 tablets containing about 0.075 mg levonorgestrel and about 0.040 mg ethinyl estradiol to be taken on consecutive days 14–18 of a menstrual cycle; 10 tablets containing about 0.125 mg levonorgestrel and about 0.030 mg ethinyl estradiol to be taken on consecutive days 19–28 of a menstrual cycle; and 7 placebo tablets containing no oral contraceptive hormones to be taken on days 1–7 of the menstrual cycle.

EXAMPLE 11

An oral contraceptive formulation comprising 28 tablets as follows: 6 tablets containing 0.03 mg ethinyl estradiol, 0.05 mg levonorgestrel and 0.25 mg methyltestosterone to be taken on consecutive days 8–13 of a menstrual cycle; 5 tablets containing about 0.075 mg levonorgestrel, about 0.040 mg ethinyl estradiol, and about 0.25 mg methyltestosterone to be taken on consecutive days 14–18 of a menstrual cycle; 10 tablets containing about 0.125 mg levonorgestrel, about 0.030 mg ethinyl estradiol 0.25 mg methyltestosterone to be taken on consecutive days 19–28 of a menstrual cycle; and 7 placebo tablets containing no oral contraceptive hormones to be taken on days 1–7 of the menstrual cycle.

EXAMPLE 12

An oral contraceptive formulation comprising 28 tablets as follows: 6 tablets containing 0.03 mg ethinyl estradiol, 0.05 mg levonorgestrel and 0.5 mg methyltestosterone to be taken on consecutive days 8–13 of a menstrual cycle; 5 tablets containing about 0.075 mg levonorgestrel, about 0.040 mg ethinyl estradiol, and about 0.5 mg methyltestosterone to be taken on consecutive days 14–18 of a menstrual cycle; 10 tablets containing about 0.125 mg levonorgestrel, about 0.030 mg ethinyl estradiol 0.5 mg methyltestosterone to be taken on consecutive days 19–28 of a menstrual cycle; and 7 placebo tablets containing no oral contraceptive hormones to be taken on days 1–7 of the menstrual cycle.

While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adams, Kaplan and Williams, "Effects of androgens on coronary atherosclerosis and atherosclerosis-related impairment of vascular responsiveness," *Arterioscler. Thromb. Vasc. Biol.*, 15:562–570, 1995.

Adashi, "The climacteric ovary as a functional gonadropin-driven androgen-producing gland," *Fertil. Steril.*, 62:20–27, 1994.

Barrett-Connor, "The economic and human costs of osteoporotic fracture," *Am. J. Med.*, 98(Suppl. 2A):3S–8S, 1995.

Bubenik, Schams and Coenen, "The effect of artificial photoperiodicity and antiandrogen treatment on the antler growth and plasma levels of LH, FSH, testosterone, prolactin and alkaline phosphatase in the male white-tailed deer," *Comp. Biochem. Physiol. A Comp. Physiol.*, 87:551–559, 1987.

Buchanan, Hospodar, Myers, Levenberger, and Demers, "Effects of excess endogenous androgens on bone density in young women," *J. Clin. Endocrinol. Metab.*, 67:937–943, 1988.

Carlson, Jayo, Jerome, Register, Weaver and Adams, "Histomorphometry and serum chemistries in surgically menopausal cynomolgus monkeys: Effects of hormone replacement therapy," (Abstract), *Bone Miner.*, 17(Suppl. 1):151, 1992.

Carlson, Tulli, Jayo, Loeser, Tracy, Mann and Adams, "Immunolocalization of noncollagenous bone matrix proteins in lumbar vertebrae from intact and surgically menopausal cynomolgus monkeys," *J. Bone Miner. Res.*, 8:71–81, 1993.

Carr, Bresau, Givens, Byrd, Barnett-Hamm and Marshburn, "Oral contraceptive pills, gonadotropin-releasing hormone antagonists, or use in combination for treatment of hirsutism: A clinical research center study," *J. Clin. Endocrin. Metab.*, 80:1169–1178, 1995.

Castro, Rose, Green, Lehner, Peterson and Taub, "Ketamine HCl as a suitable anesthetic for endocrine, metabolic, and cardiovascular studies in *Macaca fascicularis* monkeys," *Proc. Soc. Exp. Biol. Med*, 168:389–394, 1981.

Cauley, Gutai, Kuller, Scott and Nevitt, "Black-white differences in serum sex hormones and bone mineral density," *Am. J. Epidemiol.*, 139:1035–1046, 1994.

Clarkson, Shively, Morgan, Koritnik, Adams and Kaplan, "Oral contraceptives and coronary artery atherosclerosis of cynomolgus monkeys," *Obstet. Gynecol.*, 75:217–222, 1990.

Cohen-Solal, Shih, Lundy and Parfitt, "A new method for measuring erosion depth: application to the cellular mechanisms of bone loss in postmenopausal osteoporosis," *J. Bone Miner. Res.*, 6:1331–1338, 1991.

Colvard, Eriksen, Keeting, Wilson, Lubahn, French, Riggs and Spelsberg, "Identification of androgen receptors in normal human osteoblast-like cells," *Proc. Natl. Acad Sci. USA*, 86:854–857, 1989.

*Contraception Report*, 6(3):4–14, 1995, anonymous.

Cooper, Hannaford, Croft and Kay, "Oral contraceptive pill use and fractures in women: A prospective study," *Bone*, 14:41–45, 1993.

Corbett, Schey, Lehner and Green, "Standardized method for recording blood pressure in anesthetized *Macaca fascicularis*," *Lab. Anim.*, 15:37–40, 1981.

Daniel, Martin and Drinkwater, "Cigarette smoking, steroid hormones, and bone mineral in young women," *Calcif. Tissue Int.*, 50:300–305, 1992.

Duhper, Warren, Brooks-Gunn and Fox, "Effects of hormonal status on bone density in adolescent girls," *J. Clin. Endocrinol. Metab.*, 71:1083–1088, 1990.

Dupont and Plummer, "Power and sample size calculations: A review and computer program," *Controlled Clin. Trials*, 11:116–118, 1990.

Flanagan, Lea and Kendall, "Casodex reduces bone formation rate in female rats," (Abstract), *J. Bone Miner. Res.*, 10 (Suppl 1):S349, 1995.

Gambacciani, Spinetti, Taponeco, Cappagli, Piaggesi and Fioretti, "Longitudinal evaluation of perimenopausal vertebral bone loss: effects of low-dose oral contraceptive preparation on bone mineral density and metabolism," *Obstet. Gynecol.*, 83:392–396,1994.

Goldsmith and Johnston, "Bone mineral: Effects of oral contraceptives, pregnancy, and lactation," *J. Bone J. Surg.*, 57A:657–668, 1975.

Goodwin and Jerome, "Iliac biopsy for histomorphometric analysis of trabecular bone in cynomolgus monkeys and baboons," *Lab. Anim. Sci.*, 37:213–216, 1987.

Goulding and Gold, "Flutamide-mediated androgen blockade evokes osteopenia in the female rat," *J. Bone Miner. Res.*, 8:763–769, 1993.

Greendale, Edelstein and Barrett-Connor, "The effect of endogeneous sex steroids on bone mineral density in older women," (Abstract), *J. Bone Miner. Res.*, 10(Suppl. 1):S263, 1995.

Hansen, "Assessment of age and risk factors on bone density and bone turnover in healthy premenopausal women," *Osteoporosis Int.,* 4:123–128, 1994.

Hanson, Weis, Bollen, Maslan, Singer and Eyre, "A specific immunoassay for monitoring human bone resorption: quantitation of type I collagen cross-linked N-telopeptides in urine," *J. Bone Miner. Res.,* 7:1251–1258, 1992.

Hickock, Toomey and Speroff, "A comparison of esterified estrogens with and without methyltestosterone: effects on endometrial histology and serum lipoproteins in postmenopausal women," *Obstet. Gynecol.,* 82:919–924, 1993.

Hughes, Wall, Phil and Creasman, "Reproductive hormone levels in gynecologic oncology patients undergoing surgical castration after spontaneous menopause," *Gynecol. Oncol.,* 40:42–45, 1991.

Jayo, Weaver, Adams and Rankin, "Anthropometry and bone mineral status in endocrinologically manipulated female cynomolgus macaques (*Macaca fascicularis*)," (Abstract), *J. Bone Miner. Res.,* 4(Suppl 1):S181, 1989.

Jayo, Rankin, Weaver, Carlson and Clarkson, "Accuracy and precision of lumbar bone mineral content by dual-energy X-ray absorptiometry in live female monkeys," *Calcif. Tissue Int.,* 49:43840, 1991.

Jayo, Jerome, Lees, Rankin and Weaver, "Bone mass in female cynomolgus macaques: A cross-sectional and longitudinal study by age," *Calcif. Tissue Int.,* 54:231–6, 1994.

Jayo, Register, Carlson, Rankin, Siew and Sulistiawati, "Effects of thiazide and estrogen on bone in ovariectomized monkeys," (Abstract), *J. Bone Miner. Res.,* 10:S256, 1995.

Jerome, Carlson, Register, Bain, Jayo, Weaver and Adams, "Bone functional changes in intact, ovariectomized, and ovariectomized, hormone-supplemented adult cynomolgus monkeys (*Macaca fascicularis*) evaluated by serum markers and dynamic histomorphometry," *J. Bone Miner. Res.,* 9:527–540, 1994.

Johnston, Longcope and Slemenda, "The role of androgens in skeletal integrity in women," *In: Proceedings of the 4th International Symposium on Osteoporosis and Consensus Development Conference,* B. Riis and C. Christiansen, eds., Copenhagen: Osteopress, 304–305. 1993.

Kabcenell, A. I., Pomphrey, A., Barker, D. C., Cox, E., Weisfeld, V. D., Hollendonner, J. K., eds., *In: Challenges in Health Care,* Princeton: The Robert Wood Johnson Foundation, 1991.

Kanders, Lindsay and Dempster, "Determinants of bone mass in young healthy women," *In: Osteoporosis,* Proceedings of the Intentional Symposium on Osteoporosis, C. Christiansen, C. D. Amaud, BEC Nordin, A. M. Parfitt, W. A. Peck, B. L. Riggs, eds., Copenhagen: Osteopress, pp. 337–339, 1984.

Kanders, Dempster and Lindsay, "Interaction of calcium nutrition and physical activity on bone mass in young women," *J. Bone Miner. Res.,* 3:145–149, 1988.

Kanis, "Treatment of osteoporosis in elderly women," *Am. J Med.,* 98(Suppl. 2A):60S–66S, 1995.

Kasperk, Fitzsimmonds, Strong, Mohan, Jennings, Wegedal and Baylink, "Studies of the mechanism by which androgens enhance mitogenesis and differentiation in bone," *J. Clin. Endocrinol. Metab.,* 71:1322–1329, 1990.

Kasra and Grynpas, "The effect of ovariectomy on the mechanical properties of primate cortical bone," (Abstract), *Trans. ORS,* 2(17):544, 1992.

Kasra and Grynpas, "The effects of androgens on the mechanical properties of primate bone," *Bone,* 17:265–270, 1995.

Kulin, "Normal pubertal development," *In: Rudolph's Pediatrics,* 19th edition, A. M. Rudolf, J. I. E. Horman, C. D. Rudolph, eds., Norwalk, Conn.: Appleton and Lange, pp. 1665–1668, 1991.

Kuhnz, Staks and Juetting, "Pharmacokinetics of levonorgestrel and ethinyl estradiol in 14 women during three months of treatment with a tri-step combination oral contraceptive: Serum protein binding of levonorgestrel and influence of treatment on free and total testosterone levels in the serum," *Contraception,* 50:563–580, 1994.

Lea, Moxham and Flanagan, "Androstenedione protects against cancellous bone loss in the ovariectomized rat," (Abstract), *J. Bone Miner. Res.,* 10(Suppl. 1):S349, 1995.

Lindsay, Tohme and Kanders, "The effect of oral contraceptive use on vertebral bone mass in pre- and post-menopausal women," *Contraception,* 34:333–340, 1986.

Lindsay, "The burden of osteoporosis: Cost," *Am. J Med.,* 98(Suppl. 2A):9S–11S, 1995.

Looker, Johnston, Wahner, Dunn, Calvo, Harris, Heyse and Lindsay, "Prevalence of low femoral bone density in older U.S. women from NHANES II," *J. Bone Miner. Res.,* 10:796–802, 1995.

MacCann and Potter, "Progestin-only oral contraception: A comprehensive review," *Contraception,* 50(Suppl. 1):S1–S198, 1994.

Mahoney, "A study of the menstrual cycle in *Macaca irus* with special reference to the detection of ovulation," *J. Reprod. Fertil.,* 21:153–163, 1970.

Mais, Fruzzetti, Ajossa, Paoletti, Guerriero and Melis, "Bone metabolism in young women taking a monophasic pill containing 20 μg ethinyl estradiol: a prospective study," *Contraception,* 48:445–452, 1993.

Matkovic, Jelic, Wardlaw, Ilich, Goel, Wright, Andon, Smith and Heaney, "Timing of peak bone mass in Caucasian females and its implication for the prevention of osteoporosis," *J. Clin. Invest.,* 93:799–808, 1994.

Mazess and Barden, "Bone density in premenopausal women: effects of age, dietary intake, physical activity, smoking and birth-control pills," *Am. J. Clin. Nutr.,* 53:132–142, 1991.

Melton, "How many women have osteoporosis?," *J. Bone Miner. Res.,* 10:175–177, 1995.

Munoz-Torres, Quesada and Escobar-Jimenez, "Bone mass in androgen-insensitivity syndrome: Response to hormonal replacement therapy," *Calcif. Tissue Int.,* 57:94–96, 1995.

Parfitt, Simon, Villanueva and Krane, "Procollagen type I carboxy-terminal extension peptide in serum as a marker of collagen biosynthesis in bone. Correlation with iliac bone formation rates and comparison with total alkaline phosphatase," *J. Bone Miner. Res.,* 2:427436, 1987a.

Parfitt, Drezner, Glorieux, Kanis, Malluche, Meunier, Ott and Recker, "Bone histomorphometry: standardization of nomenclature, symbols and units," *J. Bone Miner. Res.,* 2:595–610, 1987b.

Pincus, "Clinical Effect of New Progestational Compounds," *In: Clinical Endocrinology I,* E. B. Astwood, ed., Grune & Stratton, Inc., New York, pp. 526–531, 1960.

Recker, Davies, Hinders, Heaney, Stegman and Kimmel, "Bone gain in young adult women," *JAMA,* 268:2403–2408, 1992.

Register, Jayo and Jerome, "Oral contraceptive treatment inhibits normal bone mineral accretion and bone metabolism in young adult female macaques," (Abstract), *J. Bone Min. Reser.,* 10(Suppl 1):S, 1995.

Rock, Garcia and Pincus, "Synthetic Progestins in the Normal Human Menstrual Cycle," *Recent Prog. Horm. Res.,* 13:323–339, 1957.

Rosenfield and Lucky, "Acne, hirsutism, and alopecia in adolescent girls. Clinical expressions of androgen excess," *Endocrinol. Metabol. Clin. North Am.,* 22:507–532, 1993.

Shively, Jayo, Weaver and Kaplan, "Body fat distribution as a risk factor for coronary artery atherosclerosis in female cynomolgus monkeys," *Arteriosclerosis,* 7:226–231, 1987.

Siegel, In: Nomparametric statistics for behavioral sciences, New York: McGraw-Hill, 1956.

Sokal RR, Rohlf FJ., eds. Biometry, 2nd ed. New York: W. H. Freeman & Co., 1981:262–264.

Speroff and Darney, *In: A Clinical Guide for Contraception,* Baltimore: Williams and Wilkins, 1992.

Stevenson, Lees, Devenport, Cust and Ganger, "Determinants of bone density in normal women: Risk factors for future osteoporosis?," *Br. Med. J.,* 298:924–8, 1989.

Takeuchi and Guggino, "Testosterone modulates calcium channels in ROS 17/2.8 bone cells," (Abstract), *J. Bone Min. Res.,* 10(Suppl. 1):S497, 1995.

Teegarden, Lyle, Proulx, Kern, McCabe, Peacock, Johnston and Weaver, "Effect of exercise intervention and oral contraceptive use on spine bone mineral density in young women," (Abstract), *J. Bone Miner. Res.,* 10(Suppl 1):S456, 1995.

Tulli, Carlson, Jayo, Fisher, Tracy and Mann, "Immunocytochemical method for the simultaneous demonstration of three proteins in EDTA decalcified, paraffin embedded bone sections," *J. Histotechnol.,* 15:93–97, 1992.

Tuppurainen, Kroger, Saarikoski, Honkanen and Alhava, "The effect of previous oral contraceptive use on bone mineral density in perimenopausal women," *Osteoporosis International,* 4:93–98, 1994.

Vanin, Lammers, MacLusky, Casper and Grynpas, "Androgens and bone density in the aged ovariectomized rat," (Abstract), *J. Bone Miner. Res.,* 10(Suppl. 1):S250, 1995.

Watts, Notelovitz, Timmons, Addison, Wiita and Downey, "Comparison of oral estrogens and estrogens plus androgen on bone mineral density, menopausal symptoms, and lipid-protein profiles in surgical menopause," *Obstet. Gynecol.,* 85:529–537, 1995.

Wiegratz, Jung-Hoffmann and Kuhl, "Effect of two oral contraceptives containing ethinyl estradiol and gestodene or norgestimate upon androgen parameters and serum binding proteins," *Contraception,* 51:341–346, 1995.

Wilson, Gordon and Collins, "Variation in ovarian steroids associated with the annual mating period in female rhesus monkeys (*Macaca mulatta*)," *Biol. Reprod.,* 27:530–539, 1982.

Wiren, Keenan and Orwoll, "Homologous regulation of the androgen receptor in human osteoblastic cells," (Abstract), *J. Bone Miner. Res.,* 10(Suppl. 1):S494, 1995.

Wright, Papadea, Willi, Pandey, Key and Bell, "Demonstration of lack of racial difference in secretion of growth hormone in premenopausal women," (Abstract), *J. Bone Miner. Res.,* 10(Suppl. 1):S447, 1995.

Yamamoto and Okada, "Clinical usefulness of low-dose oral contraceptives for the treatment of adolescent hyperandrogenemia," *Asia-Oceania J. Obstet. Gynaecol.,* 20:225–230, 1994.

what is claimed is:

1. A method of producing a desired estrogen to androgen balance in a female, comprising administering to the female a pharmaceutical composition comprising a hormonal component, wherein the hormones in the hormonal component are an estrogen, a progestin and an androgen.

2. The method of claim 1, wherein the female is using oral contraceptives.

3. The method of claim 1, wherein the female has a loss or change in ovarian secretion of an estrogen, an androgen, an estrogen precursor or an androgen precursor.

4. The method of claim 1, wherein the hormonal component includes methyltestosterone.

5. The method of claim 1, wherein the hormonal component includes from about 0.2 mg to about 1.5 mg methyltestosterone per daily dose.

6. The method of claim 1, wherein the hormonal component includes about 0.2 mg methyltestosterone per daily dose.

7. The method of claim 1, wherein the hormonal component includes about 0.25 mg methyltestosterone per daily dose.

8. The method of claim 1, wherein the hormonal component includes about 0.3 mg methyltestosterone per daily dose.

9. The method of claim 1, wherein the hormonal component includes about 0.5 mg methyltestosterone per daily dose.

10. The method of claim 1, wherein the hormonal component includes about 1 mg methyltestosterone per daily dose.

11. The method of claim 1, wherein the hormonal component includes about 1.25 mg methyltestosterone per daily dose.

12. The method of claim 1, wherein the hormonal component includes about 1.5 mg methyltestosterone per daily dose.

13. The method of claim 1, wherein the hormonal component includes ethinyl estradiol.

14. The method of claim 1, wherein the hormonal component includes about 0.030 mg ethinyl estradiol per daily dose.

15. The method of claim 1, wherein the composition is administered orally.

16. The method of claim 1, wherein the composition is administered subdermally.

17. The method of claim 1, wherein the composition is administered transdermally.

18. The method of claim 1, wherein the female has not attained peak bone mass.

19. The method of claim 1, wherein the female is premenopausal.

20. The method of claim 1, wherein the female has a loss or change in ovarian secretion of an estrogen, an androgen, an estrogen precursor or an androgen precursor due to menopause.

21. A method of preventing pregnancy in a premenopausal female comprising administering to the female a pharmaceutical composition comprising a hormonal component, wherein the hormones in the hormonal component are an estrogen, a progestin and an androgen.

22. The method of claim 21, wherein the hormonal component includes methyltestosterone.

23. The method of claim 21, wherein the hormonal component includes from about 0.2 mg to about 1.5 mg methyltestosterone per daily dose.

24. The method of claim 21, wherein the hormonal component includes about 0.2 mg methyltestosterone per daily dose.

25. The method of claim 21, wherein the hormonal component includes about 0.25 mg methyltestosterone per daily dose.

26. The method of claim 21, wherein the hormonal component includes about 0.3 mg methyltestosterone per daily dose.

27. The method of claim 21, wherein the hormonal component includes about 0.5 mg methyltestosterone per daily dose.

28. The method of claim 21, wherein the hormonal component includes about 1 mg methyltestosterone per daily dose.

29. The method of claim 21, wherein the hormonal component includes about 1.25 mg methyltestosterone per daily dose.

30. The method of claim 21, wherein the hormonal component includes about 1.5 mg methyltestosterone per daily dose.

31. The method of claim 21, wherein the hormonal component includes ethinyl estradiol.

32. The method of claim 21, wherein the hormonal component includes about 0.030 mg ethinyl estradiol per daily dose.

33. The method of claim 21, wherein the composition is administered orally.

34. The method of claim 21, wherein the composition is administered subdermally.

35. The method of claim 21, wherein the composition is administered transdermally.

36. The method of claim 21, wherein the female has not attained peak bone mass.

37. A method of increasing the level of free testosterone in the serum of a female comprising administering to the female a pharmaceutical composition comprising a hormonal component, wherein the hormones in the hormonal component are an estrogen, a progestin and an androgen.

38. The method of claim 21, wherein the female has a loss or change in ovarian secretion of an estrogen, an androgen, an estrogen precursor or an androgen precursor due to menopause.

39. A method of replacing the natural estrogen to androgen balance in a female with a deficiency or imbalance of ovarian secretions comprising administering to the female a pharmaceutical composition comprising a hormonal component, wherein the hormones in the hormonal component are an estrogen, a progestin and an androgen.

40. The method of claim 39, wherein the estrogen therapy is due to a loss or change in ovarian secretion of an estrogen, an androgen, an estrogen precursor or an androgen precursor.

41. The method of claim 39, wherein the hormonal component includes methyltestosterone.

42. The method of claim 39, wherein the hormonal component includes from about 0.2 mg to about 1.5 mg methyltestosterone per daily dose.

43. The method of claim 39, wherein the hormonal component includes about 0.2 mg methyltestosterone per daily dose.

44. The method of claim 39, wherein the hormonal component includes about 0.25 mg methyltestosterone per daily dose.

45. The method of claim 39, wherein the hormonal component includes about 0.3 mg methyltestosterone per daily dose.

46. The method of claim 39, wherein the hormonal component includes about 0.5 mg methyltestosterone per daily dose.

47. The method of claim 39, wherein the hormonal component includes about 1 mg methyltestosterone per daily dose.

48. The method of claim 39, wherein the hormonal component includes about 1.25 mg methyltestosterone per daily dose.

49. The method of claim 39, wherein the hormonal component includes about 1.5 mg methyltestosterone per daily dose.

50. The method of claim 39, wherein the hormonal component includes ethinyl estradiol.

51. The method of claim 39, wherein the hormonal component includes about 0.030 mg ethinyl estradiol per daily dose.

52. The method of claim 39, wherein the composition is administered orally.

53. The method of claim 39, wherein the composition is administered subdermally.

54. The method of claim 39, wherein the composition is administered transdermally.

55. The method of claim 39, wherein the female has not attained peak bone mass.

56. The method of claim 39, wherein the female is premenopausal.

57. The method of claim 39, wherein the female has a loss or change in ovarian secretion of an estrogen, an androgen, an estrogen precursor or an androgen precursor due to menopause.

58. A method of replacing the natural estrogen to androgen balance in a female in need of estrogen therapy, wherein the method comprises administering to the female a pharmaceutical composition comprising a hormonal component, wherein the hormones in the hormonal component are an estrogen, a progestin and an androgen.

59. The method of claim 58, wherein the estrogen therapy is a contraceptive.

60. The method of claim 58, wherein the estrogen therapy is due to a loss or change in ovarian secretion of an estrogen, an androgen, an estrogen precursor or an androgen precursor.

61. The method of claim 58, wherein the hormonal component includes methyltestosterone.

62. The method of claim 58, wherein the hormonal component includes from about 0.2 mg to about 1.5 mg methyltestosterone per daily dose.

63. The method of claim 58, wherein the hormonal component includes about 0.2 mg methyltestosterone per daily dose.

64. The method of claim 58, wherein the hormonal component includes about 0.25 mg methyltestosterone per daily dose.

65. The method of claim 58, wherein the hormonal component includes about 0.3 mg methyltestosterone per daily dose.

66. The method of claim 58, wherein the hormonal component includes about 0.5 mg methyltestosterone per daily dose.

67. The method of claim 58, wherein the hormonal component includes about 1 mg methyltestosterone per daily dose.

68. The method of claim 58, wherein the hormonal component includes about 1.25 mg methyltestosterone per daily dose.

69. The method of claim 58, wherein the hormonal component includes about 1.5 mg methyltestosterone per daily dose.

70. The method of claim 58, wherein the hormonal component includes ethinyl estradiol.

71. The method of claim 58, wherein the hormonal component includes about 0.030 mg ethinyl estradiol per daily dose.

72. The method of claim 58, wherein the composition is administered orally.

73. The method of claim 58, wherein the composition is administered subdermally.

74. The method of claim 58, wherein the composition is administered transdermally.

75. The method of claim 58, wherein the female has not attained peak bone mass.

76. The method of claim 58, wherein the female is premenopausal.

77. The method of claim 58, wherein the female has a loss or change in ovarian secretion of an estrogen, an androgen, an estrogen precursor or an androgen precursor due to menopause.

78. The method of claim 37, wherein the female has a loss or change in ovarian secretion of an estrogen, an androgen, an estrogen precursor or an androgen precursor due to menopause.

79. The method of claim 37 wherein the hormonal component includes methyltestosterone.

80. The method of claim 37, wherein the hormonal component includes from about 0.2 mg to about 1.5 mg methyltestosterone per daily dose.

81. The method of claim 37, wherein the hormonal component includes about 0.2 mg methyltestosterone per daily dose.

82. The method of claim 37, wherein the hormonal component includes about 0.25 mg methyltestosterone per daily dose.

83. The method of claim 37, wherein the hormonal component includes about 0.3 mg methyltestosterone per daily dose.

84. The method of claim 37, wherein the hormonal component includes about 0.5 mg methyltestosterone per daily dose.

85. The method of claim 37, wherein the hormonal component includes about 1 mg methyltestosterone per daily dose.

86. The method of claim 37, wherein the hormonal component includes about 1.25 mg methyltestosterone per daily dose.

87. The method of claim 37, wherein the hormonal component includes about 1.5 mg methyltestosterone per daily dose.

88. The method of claim 37, wherein the hormonal component includes ethinyl estradiol.

89. The method of claim 37, wherein the hormonal component includes about 0.030 mg ethinyl estradiol per daily dose.

90. The method of claim 37, wherein the composition is administered orally.

91. The method of claim 37, wherein the composition is administered subdermally.

92. The method of claim 37, wherein the composition is administered transdermally.

93. The method of claim 37, wherein the female has not attained peak bone mass.

94. The method of claim 37, wherein the female is premenopausal.

* * * * *